United States Patent [19]
Willner et al.

[11] Patent Number: 5,942,388
[45] Date of Patent: *Aug. 24, 1999

[54] ELECTROBIOCHEMICAL METHOD AND SYSTEM FOR THE DETERMINATION OF AN ANALYTE WHICH IS A MEMBER OF A RECOGNITION PAIR IN A LIQUID MEDIUM, AND ELECTRODES THEREOF

[75] Inventors: Itamar Willner, Mevasseret Zion; Arie Dagan, Jerusalem; Shai Rubin, Mevasseret Zion; Ron Blonder, Jerusalem; Azalia Riklin, Jerusalem; Yael Cohen, Jerusalem, all of Israel

[73] Assignee: Yissum Research Development Company of the Hebrew University of Jersaleum, Jersaleum, Israel

[ * ] Notice: This patent issued on a continued prosecution application filed under 37 CFR 1.53(d), and is subject to the twenty year patent term provisions of 35 U.S.C. 154(a)(2).

[21] Appl. No.: 08/390,978

[22] Filed: Feb. 21, 1995

[30] Foreign Application Priority Data

Feb. 22, 1994 [IL] Israel .......................................... 108726

[51] Int. Cl.⁶ ....................... G01N 33/543; G01N 33/553
[52] U.S. Cl. ................... 435/6; 204/193; 204/402; 204/403; 204/416; 204/420; 204/422; 204/280; 422/82.01; 422/82.03; 435/7.1; 435/7.8; 435/7.95; 435/962; 436/518; 436/806; 436/825; 436/524; 436/525
[58] Field of Search .................................... 204/193, 402, 204/403, 416, 420, 422, 280; 422/82.01, 82.03; 435/7.1, 6, 7.8, 7.95, 962; 436/518, 806, 825, 524, 525

[56] References Cited

U.S. PATENT DOCUMENTS

| | | |
|---|---|---|
| 4,591,550 | 5/1986 | Hafeman et al. . |
| 4,927,502 | 5/1990 | Reading et al. . |
| 4,964,972 | 10/1990 | Sagiv et al. . |
| 5,135,876 | 8/1992 | Andrade et al. . |

(List continued on next page.)

FOREIGN PATENT DOCUMENTS

| | | |
|---|---|---|
| 0 142 301 A2 | 5/1985 | European Pat. Off. . |
| 0 167 248 | 5/1985 | European Pat. Off. . |
| 0 390 390 | 3/1990 | European Pat. Off. . |
| 277 759 A1 | 12/1988 | Germany . |
| WO 90/10655 | 3/1990 | WIPO . |
| WO 90/12092 | 4/1990 | WIPO . |

OTHER PUBLICATIONS

Article Entitled: "Electrical Connection of Enzyme Redox Centers to Eelctrodes", Adam Heller; 1992 American Chemical Society; pp. 3579–3587.

Article Entitled "A glucose electrode based on a carbon paste chemically modified with a ferrocene–containing siloxane polymer and glucose oxidase, coated with a poly-(ester–sulfonic acid) cation–exchange", L. Gorton, H.I. Karan, P.D. Hale T. Inagaki, Y. Okamoto and T.A. Skotheim; 1990 Elsevier Science Publishers B.V.; pp. 23–30.

(List continued on next page.)

Primary Examiner—Christopher L. Chin
Attorney, Agent, or Firm—Blank Rome Comisky & McCauley LLP

[57] ABSTRACT

An elcctrobiochemical system for the determination of the presence and optionally concentration of an analyte in a liquid medium, the system comprising an electrode having immobilized thereon a member of a recognition pair, the other member of said pair being said analyte, the presence of said analyte in the medium resulting in formation of a pair complex, being a complex between said immobilized member and said analyte; the system further comprising redox molecules capable of changing their redox state by accepting electrons from or donating electrons to the electrode; the formation of the pair complex on the electrode bringing a change in the electrical response of the system, whereby the presence and optionally the concentration of said analyte in the medium can be determined.

32 Claims, 19 Drawing Sheets

U.S. PATENT DOCUMENTS

| | | |
|---|---|---|
| 5,198,367 | 3/1993 | Aizawa et al. . |
| 5,232,574 | 8/1993 | Saika et al. . |
| 5,246,846 | 9/1993 | Pittner et al. . |
| 5,443,701 | 8/1995 | Willner et al. . |
| 5,541,069 | 7/1996 | Mortensen et al. . |

OTHER PUBLICATIONS

Article Entitled: "Direct Electrical Communication between Chemically Modified Enzymes and Metal Electrodes. 2. Methods for Bonding Electron–Transfer Relays to Glucose Oxidase and Damino–Acid Oxidase", Yinon Degani and Adam Heller; 1988 American Chemical Society; pp. 2615–2620.

Article Enttiled: "Electron–Transfer Communication between a Redox Polymer Matrix and an Imoobolized Enzyme: Activity of Nitrate Reductase in a Viologen–Acrylamide Copolymer", Itamar Willner, Azalia Riklin and Noa Lapidot; 1990 American Chemical Society; pp. 6438–6439.

Article Entitled: "Electrically Wired Glutathione Reductase: A Biocatalyst for the Photochemical Reduction of Glutathione", Itamar Willner and Noa Lapidot; 1991 American Chemical Society; pp. 3625–3626.

Article Entitled: "Immbolization of Glucose Oxiase in Ferrocene–Modified Pyrrole Polymers", Nicola C. Fouds and Christopher R. Lowe; 1988 American Chemical Society; pp. 2473–2478.

Cover Page of Book Entitled: "Organic Chemistry A Short Course", Harol Hart (Michigan State University); Problems17.9, 17–11–13 on p. 467.

Article Entitled: "Multienzyme Membranes for Biosensors", Milka A. Krysteva & Lyubov K. Yotova; Department of Biotechnology, Technological University of Sofia, Sofia 1756, Bulgaria; pp. 13–18.

Article Entitled: "Electrical Connection of Enzyme Redox Centers to Electrodes", Adam Heller; J. Phys. Chem. 1992, 96, 3579–3587; pp. 3579–3587.

Article Entitled: "Electrical Wiring of Redox Enzymes"; Adam Heller; 1990 American Chemical Society; pp. 128–134.

Article Entitled: "Electrical Communication between Redox Centers of Glucose Oxidase and Electrodes via Electrostatically and Covalently Bound Redox Polymers", Yinon Degani and Adam Helier; 1989 American Chemical Society; pp. 2357–2358.

Article Entitled: "Mediated Electron Transfer in Glutathione Reductase Organized in Self–Assembled Monolayers on Au Electrodes", Itamar Willner, Eugenii Katz, Azalia Riklin, and Ron Kashner, 1992 American Chemical Society; pp. 10965–10966.

Article Entitled "Solid phase peptide synthesis of $^{15}$N–gramicidins A, B, and C and high performance liquid chromatographic purification," Cynthia G. Fields, Gregg B. Fields, Richcard L. Noble and T.A. Cross, Int. J. Peptide Protein Res. 33, 1989, pp. 298–303.

Article Entitled: "A Homogenous Bioelectrochemical Immunoassay for Thyroxine", G.A. Robinson, G. Martinazzo and G.C. Forrest, Journal of Immunoassay, 7(1&2), 1–15 (1986).

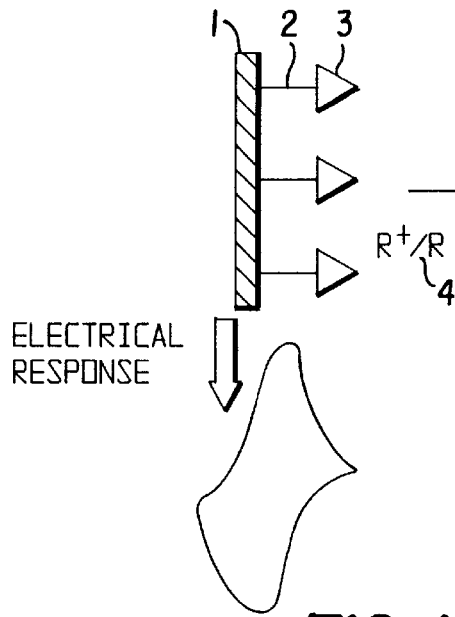
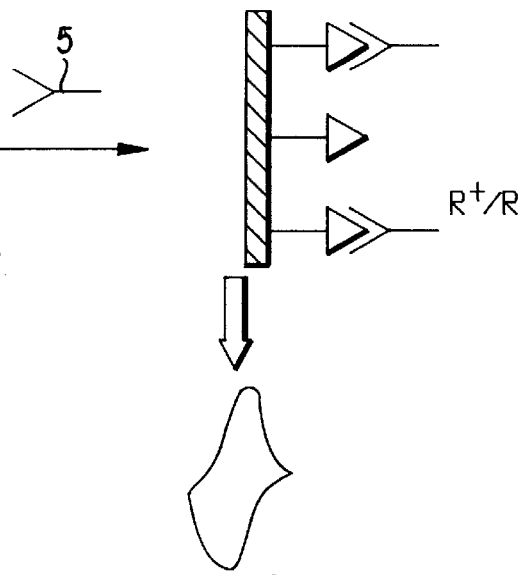
FIG. 1a    FIG. 1b
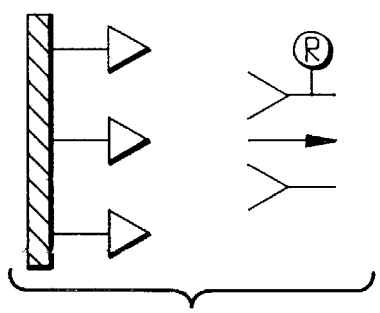
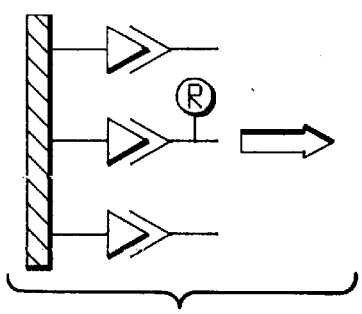
FIG. 3a    FIG. 3b    FIG. 3c
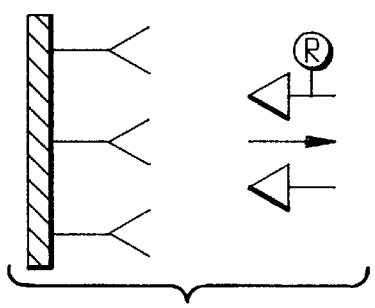
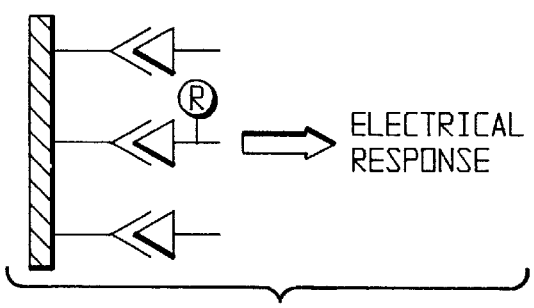
FIG. 5a    FIG. 5b

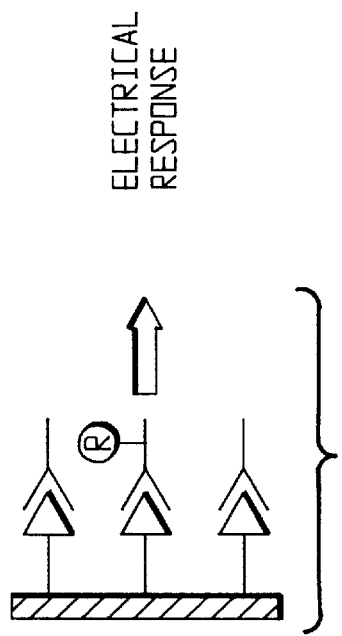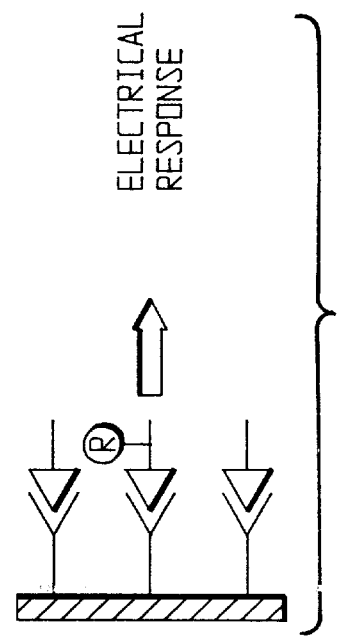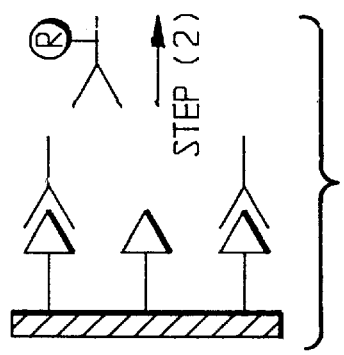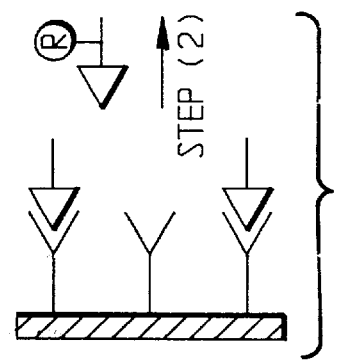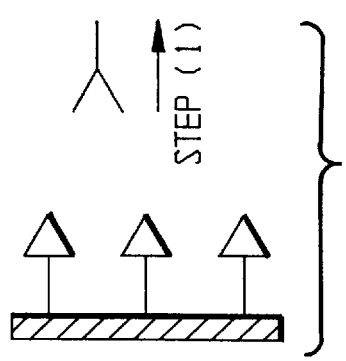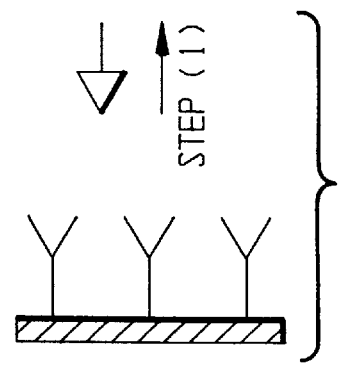

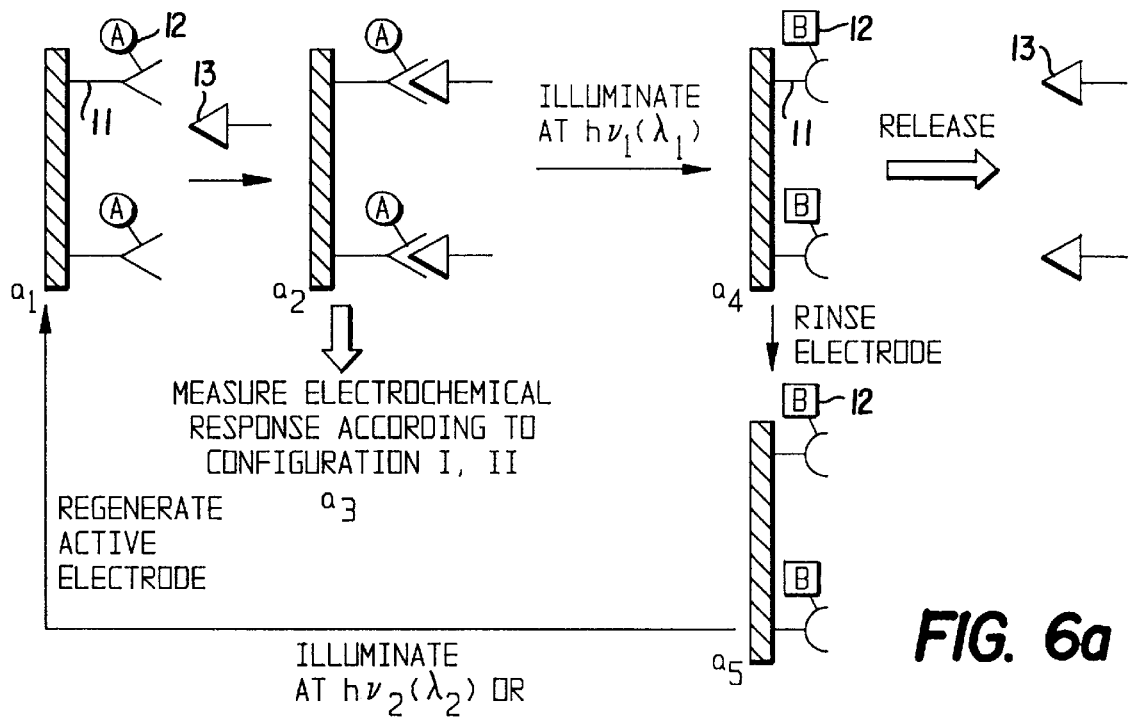
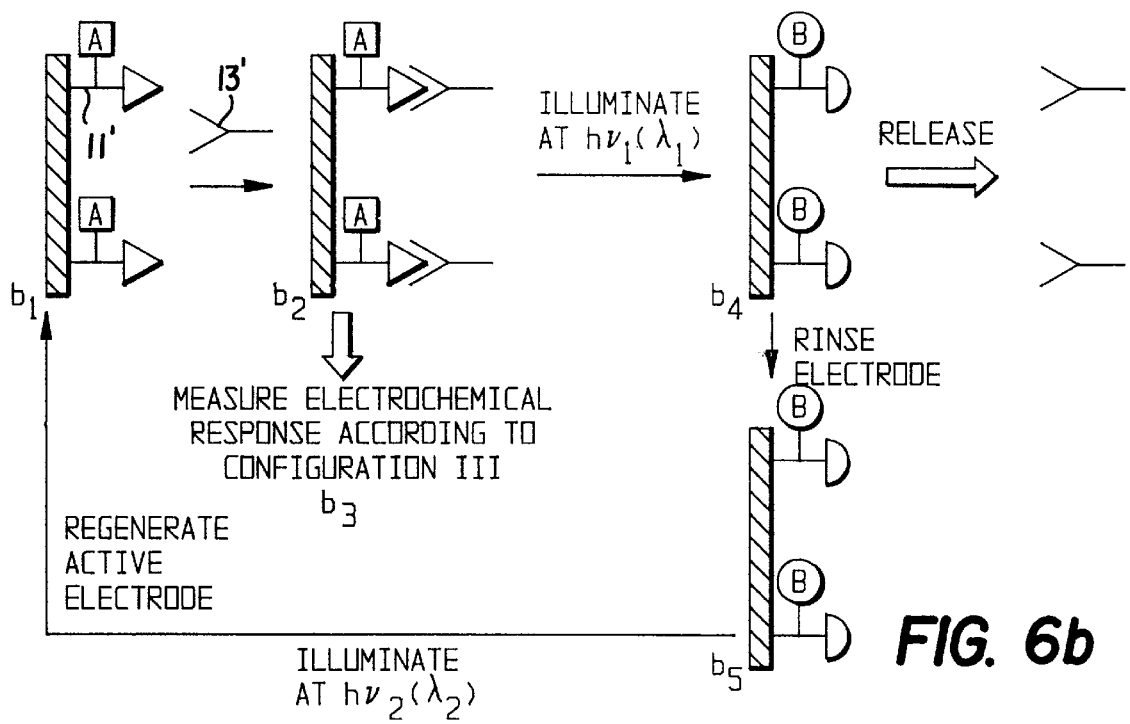
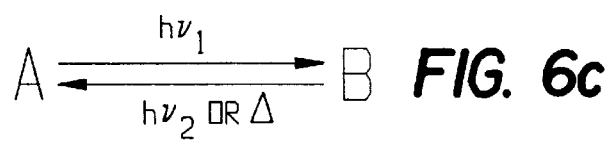
FIG. 6a
FIG. 6b
FIG. 6c

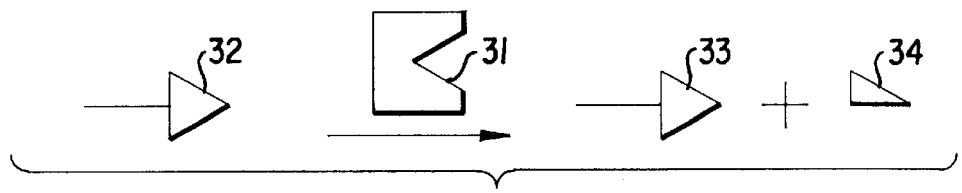
FIG. 9a
FIG. 9b
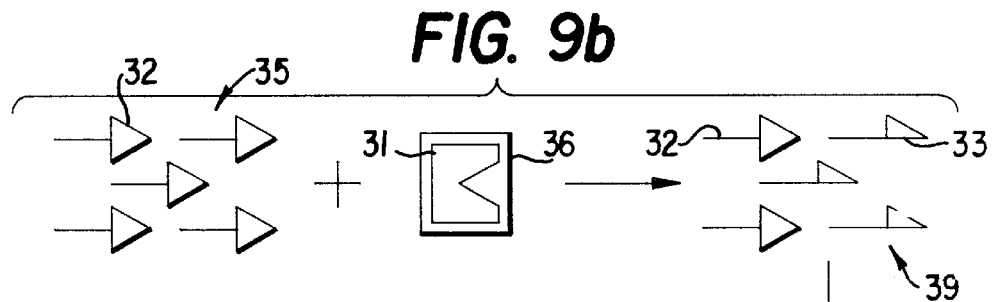
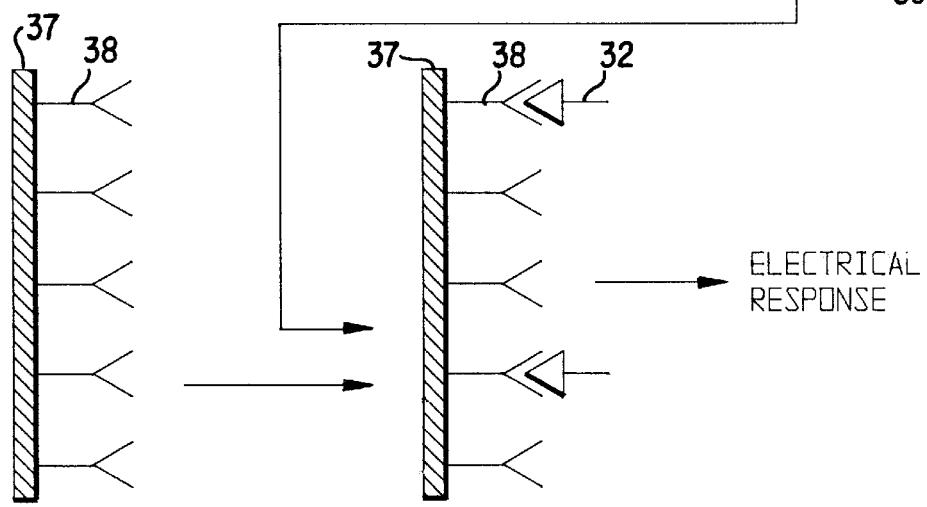
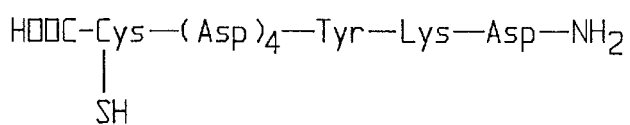
FIG. 17a
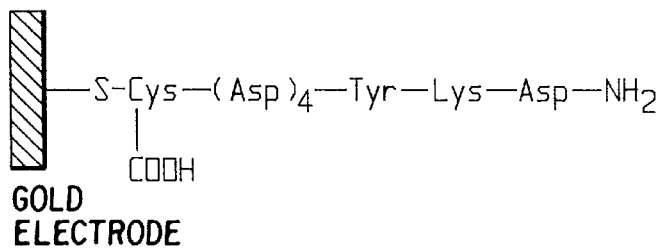
FIG. 17b

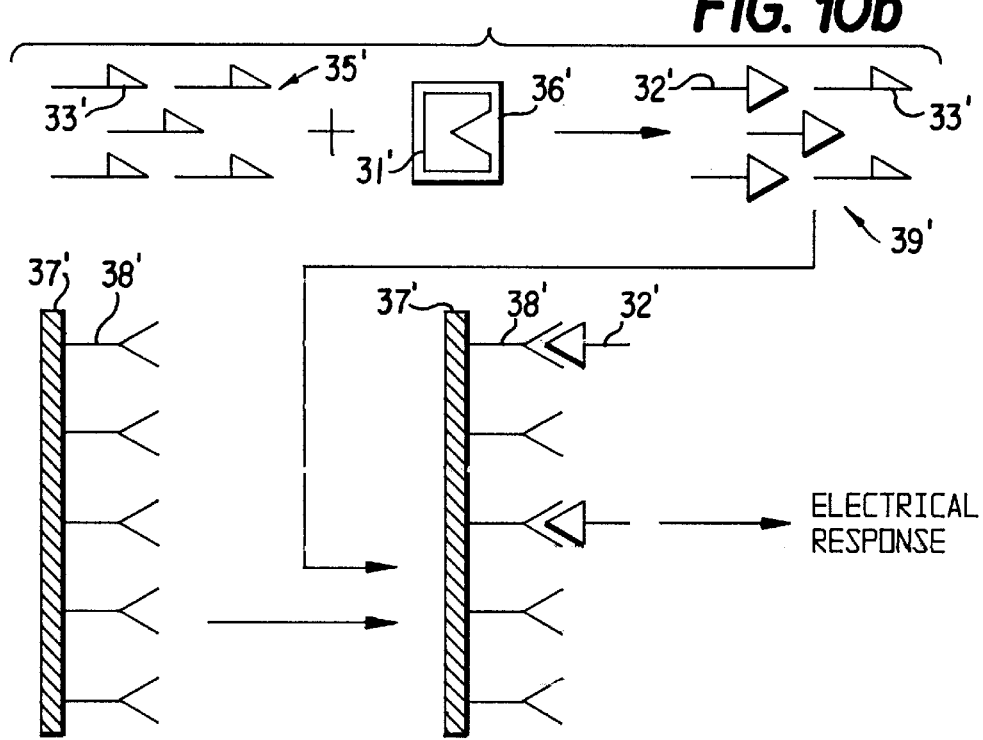
FIG. 10a
FIG. 10b
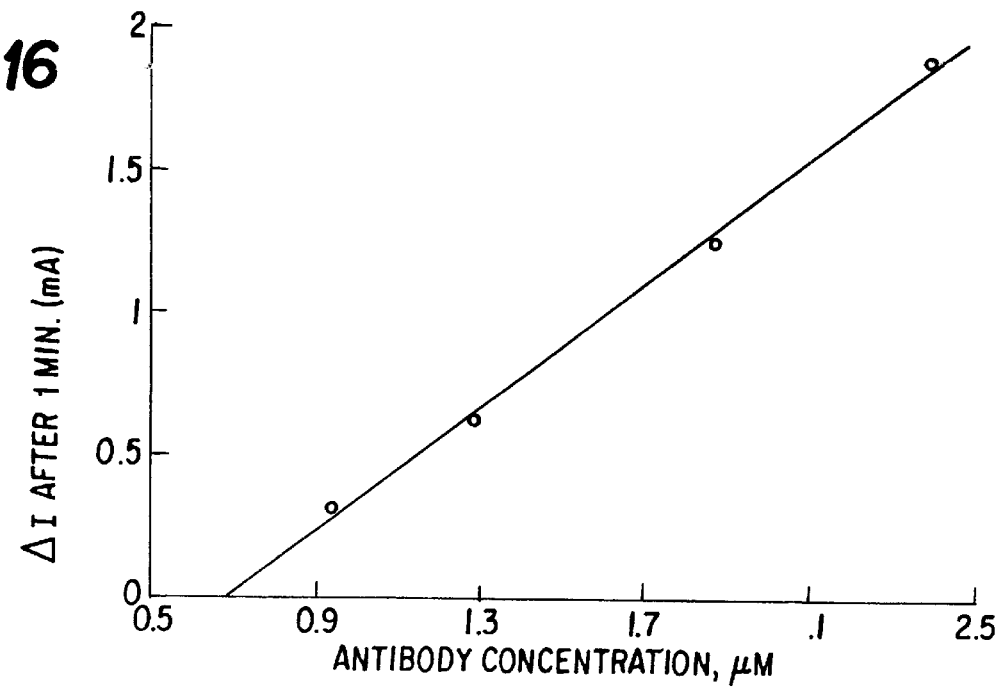
FIG. 16

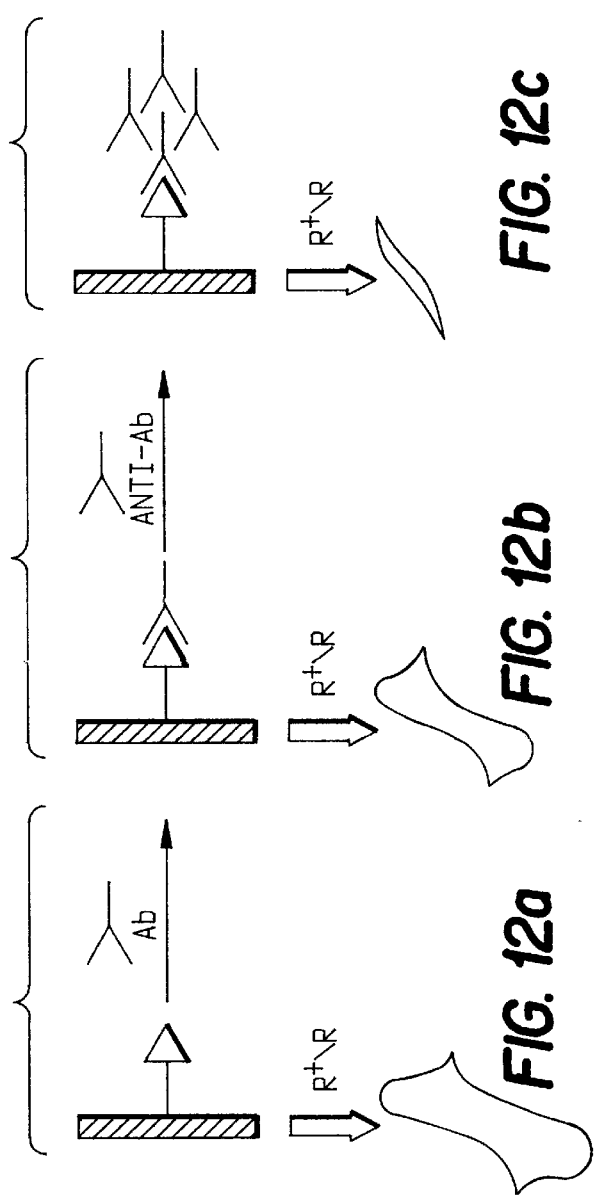
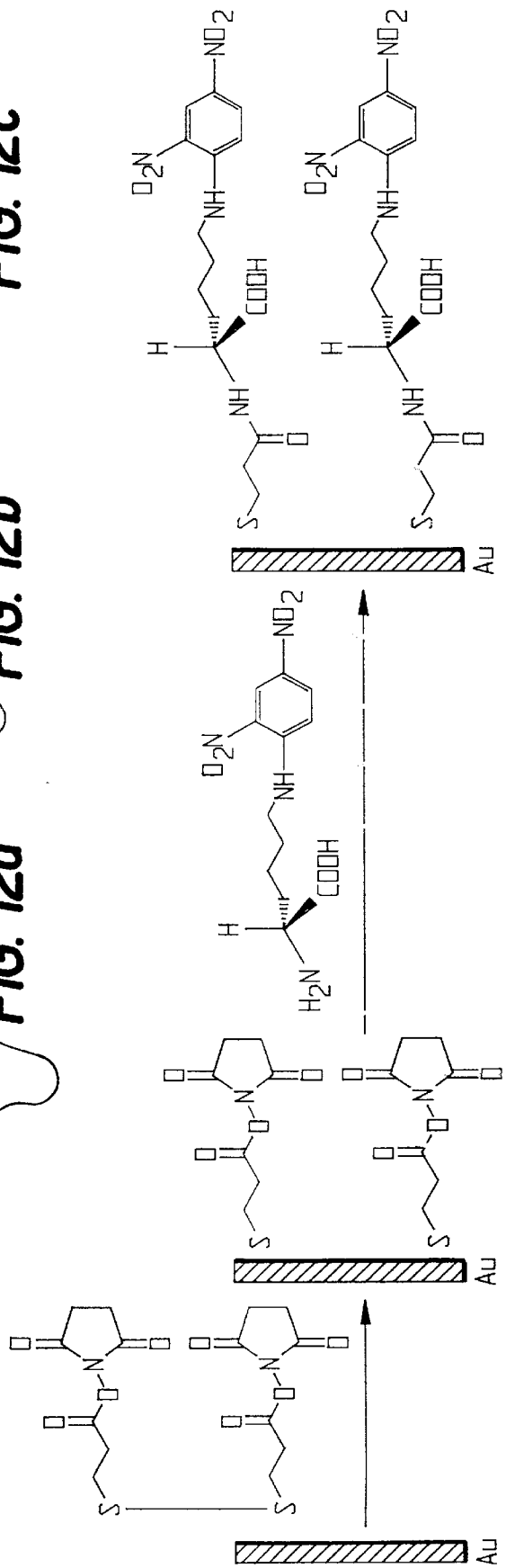
FIG. 12a
FIG. 12b
FIG. 12c
FIG. 13

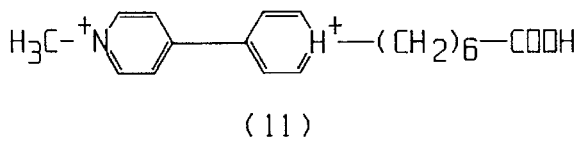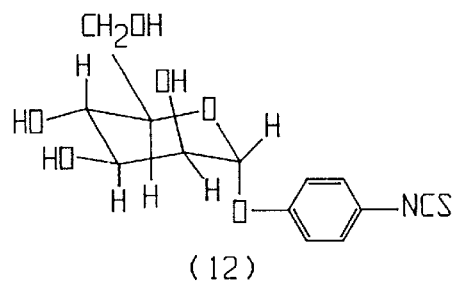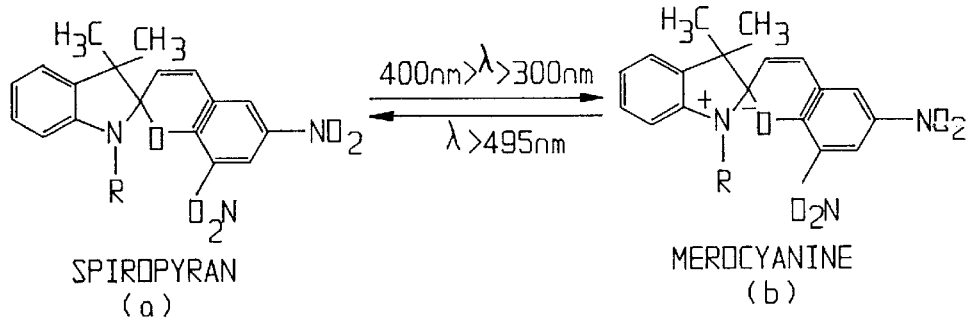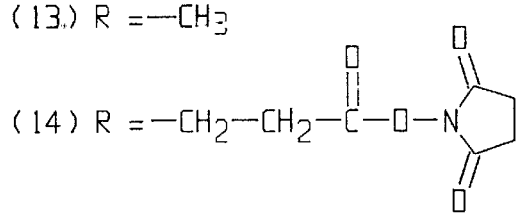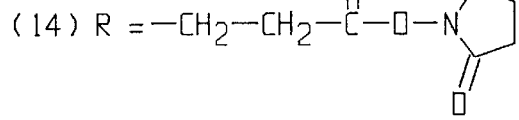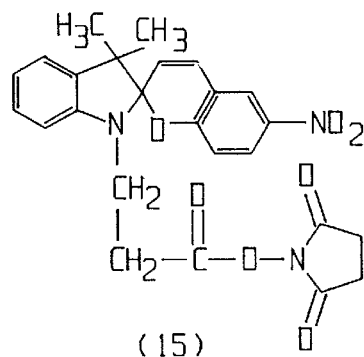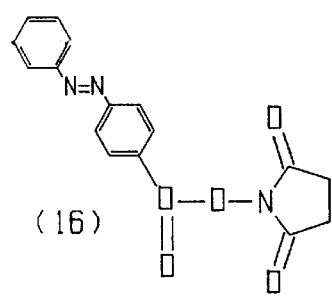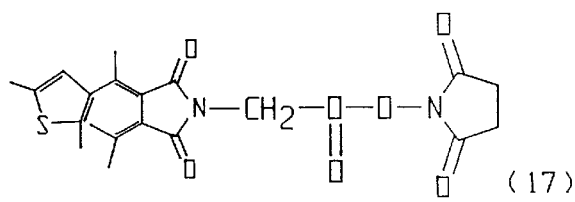
FIG. 19b

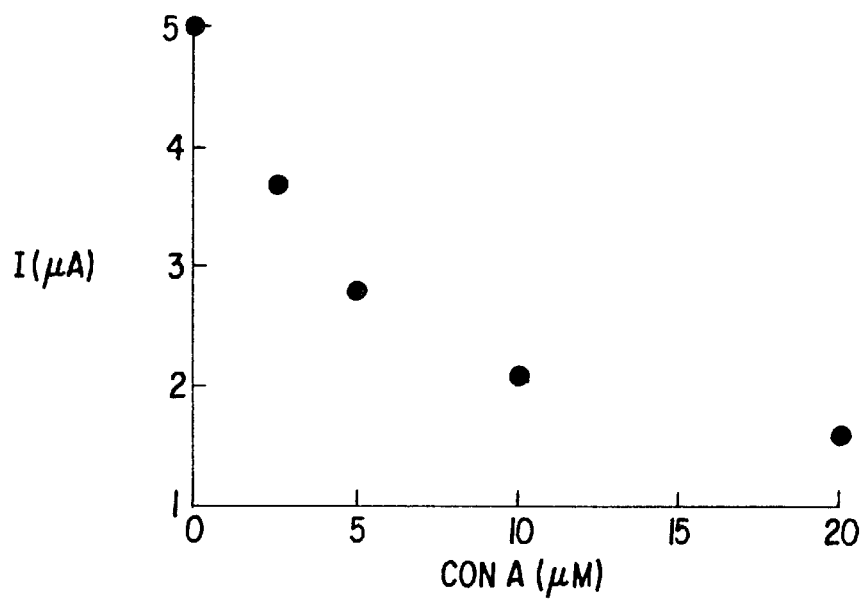
FIG. 23
FIG. 24
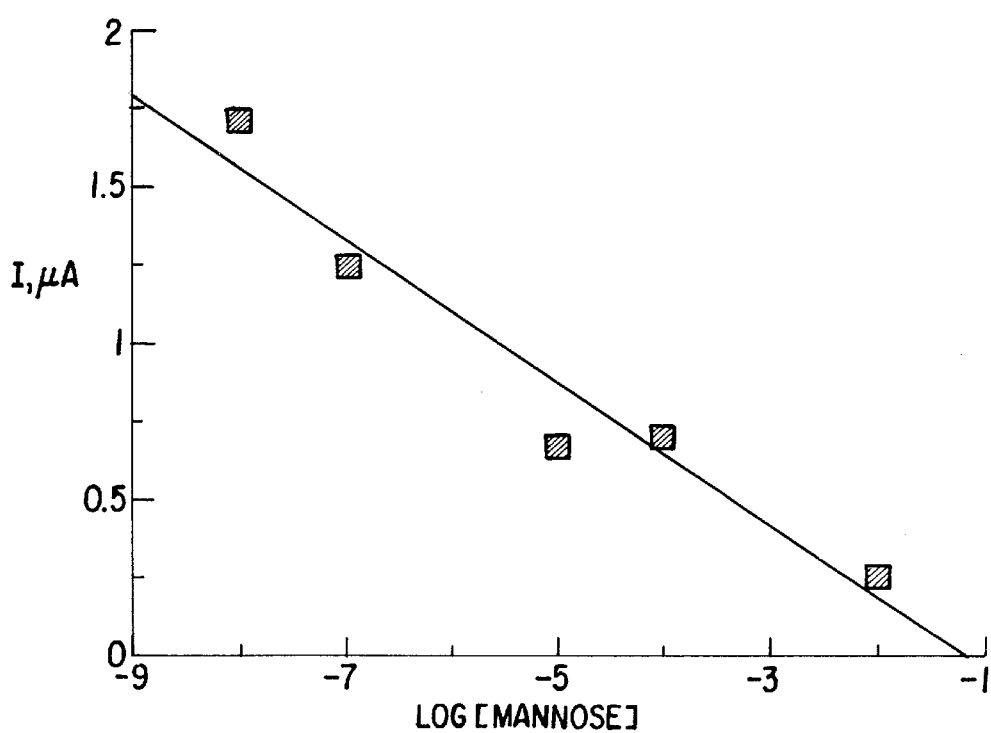

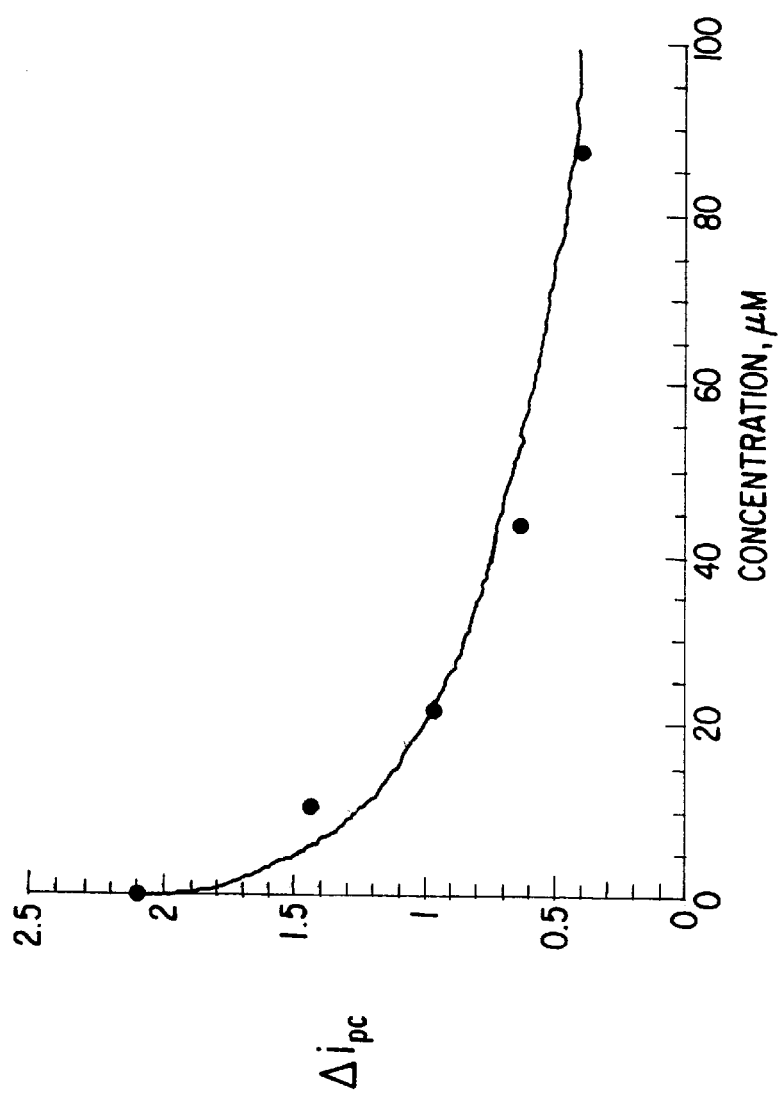
FIG. 27
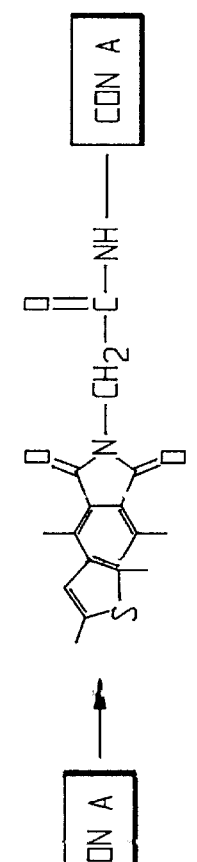
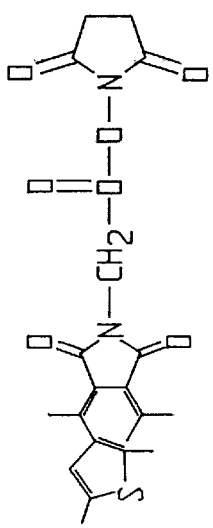
FIG. 28

3 - AMINOPROPYLTRIETHOXYSILANE

I.T.O. - INDIUM TIN OXIDE

ELECTROBIOCHEMICAL METHOD AND SYSTEM FOR THE DETERMINATION OF AN ANALYTE WHICH IS A MEMBER OF A RECOGNITION PAIR IN A LIQUID MEDIUM, AND ELECTRODES THEREOF

FIELD OF THE INVENTION

The present invention is in the field of electrobiochemical sensors and concerns a system for the determination of the presence and optionally concentration of an analyle in a liquid medium. In accordance with the present invention the analyte is determined by means of a change in the electrical response which occurs in the presence of the analyte.

BACKGROUND OF THE INVENTION AND PRIOR ART

Biosensors, based on redox enzymes, that provide an amperometric response to the enzyme specific analytes, have been proposed for the determination of analytes such as glucose, lactic acid or choline (A. Heller, *Acc. Chenz. Res.*, 23, 128 (1990) and *J. Phys. Chem.*, 96, 3579 (1992)). Another kind of assay making use of electrodes coated by redox enzymes useful for the detection of the presence and optionally concentration of an analyte in a medium has been described by I. Willner et al. (*J. Amer. Chem. Soc.*, 114, 10965–10966 (1992)). This publication describes the construction of an enzyme immobilized layer on an electrode and the electrical communication between the redox enzyme with the electrode surface by means of a diffusional electron mediator or a protein-linked electron mediator.

The use of electrochemical immunoassays involving electroactive enzyme complexes as signal amplification components has been described by G. A. Robinson et al., *J. Immunoassay*, 1–15 (1986) and in European Patent Application No. 85303367.8 (Publication No. EP 167248). This immunoassay, which involves the probing of enzyme complexes, has a major drawback in that the activity diminishes with time as well as upon the addition of ingredients which are required for the enzymatic reactions.

The use of a homogeneous electrochemical immunoassay is disclosed in U.S. Pat. No. 5,198,367. This assay involves the preparation of an antigenic redox active protein complex, wherein the electrical communication of the complex with the electrode in the presence of the respective antibody is controlled by the analyte in the solution. The preparation of the three component antigenic-redox relay protein complex is difficult. Furthermore, all electrochemical immunoassays are single-cycle sensing devices and cannot be reused: after a single measurement the activity of the probing complexes is terminated.

Electrobiochemical sensors for the detection of redox inactive biomolecules and particularly biomolecules appearing in sub-micromolar and nanomolar concentration ranges, have important potential applications in diagnostics, food analysis and environmental analysis. Examples can range from detecting antibodies and antigens to tracing undesirable metabolites and herbicides to identifying the presence of toxins and viruses.

It is an object of the present invention to provide an electro-biochemical system for the determination of the presence and optionally the concentration of an analyte in a liquid medium, the analyte being a member of a recognition pair.

It is further an object in accordance with an embodiment of the present invention to provide an electrobiochemical system as above which is substantially reversible and reusable.

It is furthermore the object of the present invention to provide electrodes for use in the above systems.

It is still a further object of the present invention to provide a process for the preparation of such electrodes.

GENERAL DESCRIPTION OF THE INVENTION

In the following description the term "electrical response" will be used to denote the current-voltage behavior of the electrode, e.g. the current or charge flow under a certain potential. The electrical response may be determined by measuring current or charge flow.

In accordance with the present invention a novel electrobiochemical system and an electrode for use in the biochemical system is provided. The system in accordance with the invention is capable, by means of a change in electrical response of an electrobiochemical electrode, to determine the presence and optionally the concentration of an analyte in a liquid medium. The analyte forms a part of a recognition pair, for example, an antigen-antibody, ligand-receptor, sugar-lectin, biotin-avidin, enzyme-substrate, oligonucleotide-DNA, oligonucleotide-protein, and olignucleotide-cell.

In accordance with the first aspect of the invention there is provided an electrobiochemical system for the determination of the presence and optionally concentration of an analyte in a liquid medium, the system comprising an electrode having immobilized thereon a member of a recognition pair, the other member of said pair being said analyte, the presence of said analyte in the medium resulting in formation of a complex between said immobilized member and said analyte (hereinafter: "pair complex"); the system further comprising redox molecules capable of changing their redox state by accepting electrons from or donating electrons to the electrode; the formation of the pair complex on the electrode bringing a change in the electrical response of the system, whereby the presence and optionally the concentration of said analyte in the medium can be determined.

The immobilized member may be a member of any specific recognition pair. Examples of such recognition pairs are antigen-antibody, sugar-lectin, ligand-receptor, biotin-avidin, enzyme-substrate, oligonucleotide-DNA, oligonucleotide-protein, and oligonucleotide-cell. When one of such a pair, e.g. an antigen, is immobilized on the electrode, it then is suitable for the determination of the other member of the recognition pair in a liquid medium, e.g. in the antibody.

As a result of binding of the analyte onto the electrode and the formation of a pair complex consisting of the two members of the recognition pair immobilized on the electrode, there results a change in electrical response of the electrodes which provides an indication of the presence of said analyte in the medium. The degree of change in the electrodes' electrical properties correlates with the extent of binding of said analyte to the immobilized member and is dependent upon the concentration of said analyte in the medium surrounding the electrode. Thus, the extent of change in the electrical properties may be used, by a preferred embodiment of the invention, as an indication of the concentration of said analyte in the medium.

In the following description the term "determination" will be used collectively to denote both determination of only the presence or determination of both the presence and concentration in a liquid medium.

The invention is useful for the determination of an agent in a biological sample, an aquatic sample or food sample.

The determination may be carried out by one of two modes to be referred to herein as the "direct mode" and the "indirect mode ". In accordance with the direct mode, the agent in the biological sample is the analyte of the system. In accordance with the indirect mode, the agent and the analyte are different; the analyte which is determined in said system serves as a measure for the determination of the agent in said sample.

The determination of an agent in a biological sample in accordance with the direct mode is essentially a single step procedure in which the electrode in said system is challenged with the tested biological sample or with an appropriate fraction thereof which contains said agent. An example of the direct mode of the invention is the determination of an antibody in a biological sample wherein the electrode has immobilized thereon an antigen to which said antibody specifically binds; or the determination of an antigen by the use of an electrode having immobilized thereon an anti-antigen antibody.

In accordance with the indirect mode, the agent in the biological sample is not determined directly but rather indirectly by an essentially two-step procedure. In accordance with this mode the biological sample is reacted, in a first step, with a reagent solution. This reaction brings to either formation of said analyte in a manner dependent on the concentration of said agent in said sample; or reduction in the concentration of said analyte present a priori. Thus, depending on the type of reaction, the concentration of the analyte will be in a direct or inverse correlation to the concentration of said agent in said sample. In a second step, the electrode is challenged with the reaction product of the first step and the analyte which is then determined will serve as an indirect measure of said agent in said sample.

By one embodiment of the indirect mode, the analyte is a molecule which binds to the tested agent. The reagent solution of this embodiment comprises the analyte and following the reaction between the reagent solution and the biological sample the analyte will bind to said agent. Consequently, the concentration of the free analyte in the solution will be reduced, i.e. the concentration of the analyte to be subsequently determined will be in an inverse correlation to the concentration of said agent in said sample.

A specific example is the use of immobilized antigen in order to determine an identical or related antigen in a biological sample to be tested. In accordance with this specific example, the biological sample, e.g. a plasma sample is first reacted with a reagent solution comprising an antibody which specifically binds to the antigen to be determined. After binding, the concentration of free antibody becomes lower. Following an incubation period, an electrode on which there is immobilized the said antigen is challenged with the reacted solution, and the determination of the free antibody serves then as an indication of said antigen in the tested biological sample. As will no doubt be appreciated by the artisan, the concentration of said free antibody will be in opposite correlation to the concentration of the antigen in the tested sample.

Furthermore, as will also be appreciated, an antibody in a tested biological sample rather than an antigen may be determined in an analogous manner, mutatis mutandis.

In accordance with another embodiment of the indirect mode, the tested agent is an enzyme and the analyte is either a molecule which is broken down by the enzyme or a molecule which is catabolized by the enzyme from another, precursor molecule. In the first case, the reagent solution comprises said analyte and following reaction with the tested sample the concentration of the analyte will be reduced in correlation with the enzyme's concentration in the sample. In the latter case, the reagent solution will comprise said precursor molecule and following reaction with the tested sample, the analyte will form and its concentration will then be in direct correlation to the enzyme's concentration in the sample.

In accordance with a further embodiment of the indirect mode, the reagent solution comprises an enzyme which converts the agent in said sample into said analyte.

In the above two embodiments, the enzyme of the testing sample in the first case or the enzyme of the reagent solution in the second case, should be removed after performance of the first step of the procedure.

By one embodiment of the invention, the redox molecules are freely tumbling in the medium. In accordance with this embodiment, upon binding of said analyte to the immobilized member the surface of the electrode is insulated or partially insulated towards the redox molecules depending upon the concentration of said analyte in liquid medium.

In accordance with another embodiment of the invention, the redox molecule is linked to analyte molecules (hereinafter at times "modified analyte"). In accordance with this embodiment, the modified analyte and the analyte originating in the tested sample compete on binding to the immobilized member. In the presence of relatively large concentrations of said analyte in the sample, there will be little binding of the modified analyte to the electrode immobilized member. In contrast, in the case of low concentrations of the analyte to be determined in a sample there will be extensive binding of the modified analyte to the immobilized member on the electrode. Binding of the modified analyte to the immobilized member brings the redox molecule into proximity with the electrode material which facilitates electron exchange between the two. Thus, upon binding of the modified analyte to the immobilized member, there will be an increase in the electrical response of the electrode. This increase will be in reverse correlation to the concentration of the analyte in the tested sample such that a large increase will indicate a small concentration of the analyte and vice versa.

In accordance with one variation of the above embodiment, the electrode is simultaneously challenged by the modified analyte and with the analyte to be determined in the sample.

In accordance with another variation of carrying out this embodiment, the electrode is first challenged with the sample in which the presence of the analyte is to be determined and subsequently challenged with a solution containing the modified analyte.

The electrode material may, be selected from a variety of conducting substances, particularly such having the capability to associate chemically with, attach or chemisorb a sulphur-containing moiety. The electrode material is preferably made of or coated by metals such as gold, platinum, silver or copper. In another embodiment the electrode may comprise of conducting glass electrodes, for example, Indium tin oxide (ITO) with functionalized alkoxysilanes associated with the electrode's surface. (Silanization of an ITO electrode can be adhered by refluxing the electrode in an argan atmosphere with 3-aminopropyltriethoxysilane in dry toluence and then drying in an oven).

The redox molecule is a molecule capable of changing its redox state by accepting or donating electrons. An example of a redox molecule is $K_4Fe(CN)_6$ [ferricyanide/ferrocyanide]. Another example is N-methyl—N'-carboxymethylene-4'4'-bipyridinium.

The immobilized member is preferably immobilized on the surface of the electrode by means of a linking group, which typically may have the following general formula (I):

$$Z—R^1—Q \quad (I)$$

wherein:

Z in case where the electrode material is one of said metals, represents a sulphur-containing moiety which is capable of chemical association with, attachment to or chemisorption onto said metal; and in case where the electrode material is glass, represents methoxy or alkoxy silane residues which are capable of chemical association, attachment to or chemisorption onto said glass;

$R^1$ represents a connecting group;

Q is a functional group which is capable of forming a covalent bond with a moiety being a member of a recognition pair.

Z where the electrode material is a metal may for example be a sulphur atom, obtained from a thiol group or a disulphide group, a sulphonate or sulphate groups.

$R^1$ may be a covalent bond or may be a peptide or polypeptide or may be selected from a very wide variety of suitable groups such as alkylene, alkenylene, alkynylene, phenyl containing chains, and many others.

Particular examples of $R^1$ are a chemical bond or a group having the following formulae (IIa), (IIb) or (IIc)

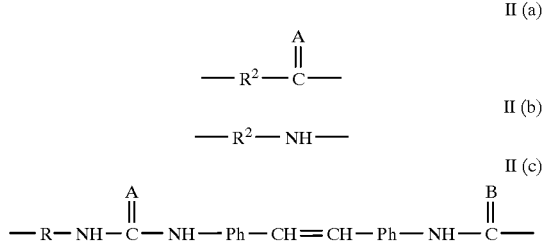

wherein $R^2$ or $R^3$ may be the same or different and represent straight or branch alkylene, alkenylene, alkynylene having 1–16 carbon atoms or represent a covalent bond, A and B may be the same or different and represent O or S, Ph is a phenyl group which is optionally substituted, e.g. by one or more members selected from the group consisting of $SO_3-$ or alkyl groups.

Q may for example be a functional group capable of binding to a carboxyl residue of a member of a recognition pair such as an amine group, a carboxyl group capable of binding to amine residues of the member of a recognition pair; an isocyanate or isothiocyanate group or an acyl group capable of binding to an amine residue of the member of a recognition pair; or a halide group capable of binding to hydroxy residues of the protein or a polypeptide. Particular examples are the groups $—NH_2—COOH$; $—N=C=S$; $N=C=O$; or an acyl group having the formula $—R^a—CO—G$ wherein G is a halogen such as Cl or OH, $OR^b$, a

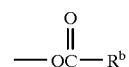

group or a

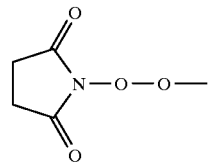

group; $R^a$ and $R^b$ being, independently a $C_1–C_{12}$ alkenyl, alkenyl or a phenyl containing chain which is optionally substituted, e.g. by halogen.

Particular examples of such a linking group are cysteamine (III), cystamine (IV) and cysteic acid N-hydroxysuccinimiole ester (V) having the formulae:

| Z | $R^1$ | Q | |
|---|---|---|---|
| HS— | $CH_2—CH_2—$ | $NH_2$ | (III) |
| S— | $CH_2—CH_2—$ | $NH_2$ | (IV) |
| \| | | | |
| S— | $CH_2—CH_2—$ | $NH_2$ | |

(V)

[Structure V: succinimide ester structure]

Binding of two members of a binding couple to one another is typically a high affinity binding, namely the two members do not dissociate easily from one another and even after the electrode is rinsed, the analyte still remains substantially bound to the immobilized member. In order to re-use the electrode for a further measurement, there is a need to dissociate the analyte from the immobilized member and remove the analyte from the system. In accordance with a preferred embodiment of the invention, the dissociation is achieved by means of a group, attached to the member immobilized on the electrode which has two isomerization states and is capable of switching reversibly between its two states by exposure to light energy at two different wavelengths. Such a group will typically have a first and second isomerization state and by reversibly switching from one state to the other will cause a conformational change in the immobilized member which will bring about a change in the binding of affinity of the immobilized member to said analyte. Such a conformational change may, for example, be the occlusion of the binding site or a conformational change within the binding site which will cause a reduction in the binding affinity of the immobilized member to the analyte which may hereinafter be defined as change or switch from a state of high affinity to a state of low affinity.

In the first state, the immobilized member will have a high affinity to binding to said analyte and after performing a measurement, the electrode will be treated so that said group will switch to the second state and consequently said analyte will dissociate from the immobilized member. After removal of said analyte from the system, typically by rinsing and washing away of the rinsing solution, the electrode will be further treated so that said group switches back to said first state, whereby the electrode will be ready for re-use.

The switching between the two states is achieved by exposure to light of an appropriate wavelength within the infra red, visible or ultra violet range. The reactive group will switch from said first state to said second state by exposure to light energy at a first wavelength and from a second state to said first state by exposure to a second, different than the first, wavelength. It is also possible that one of the switches will be achieved by mild thermotreatment.

Thus there is provided according to an embodiment of the invention a system wherein the immobilized member of the recognition pair has or is linked to a group reactive to exposure to light energy; said group having a first and a second state and is capable of being converted from the first state to the second state by exposure to irradiation of light of a first wavelength and from the second to the first state by exposure to irradiation of light of a second wavelength; the exposure inducing a change in affinity of the immobilized member for binding to said analyte, whereby in the first state said immobilized member has a high affinity of binding to said analyte such that the analyte remains essentially bound to the immobilized member and in said second state said immobilized member has a low affinity of binding to said analyte, such that the bound analyte is readily dissociated.

There is also provided according to another embodiment of the invention a system wherein the said switching from the first state to the second state is by exposure to light energy but the switching from said second state to said first state is by mild thermal treatment.

The sensitivity of the system of the invention may be increased by the use of analyte molecules which are conjugated or complexed with a large molecule or a group of molecules (hereinafter at times "complexed analyte"). The binding to the immobilized member, the complexed analytes sterically impede access of redox molecules to the electrode material. By one embodiment, this is achieved by the use of analytes conjugated to a large molecule or complex of molecules, such as for example, an antiantibody to an analyte antibody, an antibody to a protein analyte, and the like.

By another embodiment, after the analyte is allowed to bind to the immobilized member, the electrode is challenged with agents capable of binding to the bound analyte, whereby the agents complexed with the bound analyte give rise to steric impedance. In order to increase the steric impedance, after the formation of an initial complex, the electrode is reacted with anti-agents which bind or are complexed to the agents already bound or complexed to the immobilized analyte, e.g. an anti-antibody and this brings about an increase in the size of the complex and hence also an increase in the steric impedance.

By increasing the sensitivity of the system in the manner described above, a change in the electrical response of the electrode can be measured after binding of only a few analyte molecules to the electrode.

In accordance with another aspect of the invention there is provided an electrode for use in the above electrobiochemical systems for the determination of the presence and optionally concentration of an analyte in a liquid medium, the electrode comprising an electrode material having immobilized thereon a layer of a member of a recognition pair, the other member of said pair being said analyte, the electrode material being capable of electrical communication with a redox molecule, the electrical communication being modified by the binding of said analyte to the immobilized member, whereby the presence and optionally the concentration of said analyte in a medium surrounding the electrode can be determined.

By an embodiment of the invention there is provided a substantially reusable electrode for use in the above electrobiochemical system for the determination of the presence and optionally concentration of an analyte in a liquid medium, the electrode comprising an electrode material capable of electrical communication with a redox molecule; there being immobilized on the electrode material a layer of a member of a recognition pair the other member of the pair being said analyte; the electrical communication between the redox molecule and the electrode material being modified by binding of said member to said analyte; the immobilized member has or is linked to a group reactive to exposure to light energy, said group having a first and a second state and is capable of being converted from the first state to the second state by exposure to irradiation of light of a first wavelength and from the second to the first state by exposure to irradiation of light of a second wavelength; the exposure inducing a change in affinity of the immobilized member for binding to said analyte, whereby in the first state said immobilized member has a high affinity of binding to said agent such that the bound analyte is not readily dissociated and in said second state said immobilized member has a low affinity of binding to said analyte, such that the bound agent is readily dissociated and can be removed from the system and the electrode can then be exposed to light of a second wavelength inducing a change to said first state, whereby the electrode will be ready for re-use, whereby the presence and optionally the concentration of said analyte in a medium surrounding the electrode can again be determined.

The group responsive to exposure to light energy, in accordance with the preferred embodiment of the invention, is a compound having more than one stable structure or isomeric state which is sensitive to irradiation of light at a first wavelength such that it changes from a first state to a second state. This change in state is reversible as the group is also sensitive to irradiation of light at a second wavelength (or by thermal treatment) such that it changes from the second state to the first state. Typically, the first and second wavelengths are within the infra red, visible or ultra violet regions.

Examples of five families of compounds which could be used to make the group can be seen in FIG. 19—structures (1) to (5) inclusive, namely: azobenzenes (1), spiropyranes (2), fulgides (3), thiophenefulgides (4) or malachite green (5). Examples of the structural change in three of these five families of compounds which occurs upon their exposure to irradiation of light energy of an appropriate wavelength is illustrated by structures (6) to (8) of FIG. 19. Specifically item (6) exemplifies azobenzenes, structure (7) spiropyranes and structure (8) malachite green. These compounds all require structural modification to prepare a group which can be linked to the member of a recognition pair to be immobilized on the surface of the electrode. Accordingly, in the preferred embodiment these compounds are modified chemically to form active esters, amine, carboxylic acid, or halide derivatives. The presence of these moieties facilitates linkage of the group to the member of the recognition pair. Structures (13) and (14) illustrate both the appropriate wavelengths of light energy required to change spiropyran from a first state (a) to a second state (b) in which it is in its merocyamine form and also the structures of the first and second isomer states with and without the N-hydroxysuccinimide ester moiety.

The examples of photoisomerizable active esters which can be seen in FIG. 19 are N-hydroxyoxsuccinimide ester of N-propionic acid spiropyran (15), N-hydroxyoxsuccinimide ester of 4-carboxy azobenzene (16) and N-hydroxyoxsuccinimide, ester of thiophenefulgide (17).

The present invention also provides a process for preparing the above electrode, comprising:

(a) immobilizing said connecting group onto the electrode material by chemical association attachment or chemisorption of the sulphur-containing moiety or functionalized alkoxysilane to the metal or glass electrode material, respectively; and (b) binding the member of the recognition pair to be immobilized to said functional group of the connecting group.

Steps (a) and (b) may also be reversed so that immobilization takes place before binding.

The present invention further provides a process for preparing the above electrode incorporating the group reactive to light energy comprising:

(a) immobilizing said linking group onto the electrode material by chemical association attachment or chemisorption of the sulphur-containing moiety or functionalized alkoxysilane to the metal or glass electrode material, respectively;

(b) chemically modifying a member of said recognition pair with a photoisomerizable group whereby the modified member changes its bonding affinity to the other member of the recognition pair by exposure to light energy; and (c) binding the modified member of the recognition pair to said functional group of the linking group immobilized on the electrode.

Steps (b) and (c) can be reversed such that the isomerizable group is bound to the member of the recognition pair after it has been immobilized in the electrode and so can steps (a) and (b).

The invention will now be illustrated in the following description of some specific embodiments, with occasional reference to the annexed drawings, without prejudice to the generality of the aforegoing.

DESCRIPTION OF THE DRAWINGS

In the drawings:

FIG. 1 is a schematic representation of the surface of an electrode according to an embodiment in accordance with the direct mode of the invention in which a member of a recognition pair is immobilized on the surface of an electrode (a) that is immersed in liquid medium containing redox molecules $R^+/R$ and is then challenged with a solution containing an unknown concentration of the analyte member of the recognition pair which then binds to its counterpart member of the recognition pair immobilized on the said surface (b). The binding brings to a decrease of the electric response.

FIG. 2 is a schematic representation of another embodiment of the direct mode of the invention in which a member of a recognition pair is immobilized on the surface of an electrode (a) and is challenged sequentially by a solution containing an unknown concentration of the analyte member of the recognition pair (step (1)). Binding of some of the immobilized sites by the analyte takes place (b) and the electrode is then challenged by the analyte modified by linking thereto a redox molecule R (step (2)). Binding by the said modified analyte (c) produces an electrical response (d): the magnitude of the electrical response depends on the number of vacant sites remaining after step 1 which in turn depends on the analyte's concentration.

FIG. 3 is a schematic representation of a variation of the embodiment of FIG. 2, in which a member of a recognition pair is immobilized on the surface of an electrode and is then challenged simultaneously with both (i) a solution containing an unknown concentration of the analyte member of the recognition pair and (ii) the analyte member modified by linking thereto a redox molecule (a). Competitive binding dependent upon the respective concentrations of analyte and modified analyte takes place to produce an electrical response (b) leading eventually to an electrical response (c), which depends on the concentration of (i).

FIGS. 4 and 5 are schematic representations of embodiments similar to FIGS. 2 and 3, respectively, in which the analyte of FIGS. 2 and 3 is the immobilized member whereas the immobilized member of FIGS. 2 and 3 is now the analyte.

FIG. 6 is a schematic representation of a further embodiment of the direct mode of the invention in which the immobilized member is modified by linking thereto a group reactive to exposure to light energy. This group has two isomerization states, indicated in the drawings as A and B and as illustrated in FIG. 6(c) it switches from A to B by exposure to light energy $hv_1$, and switches back from B to A by exposure to light energy $hv_2$. By exposure to light of an appropriate wavelength, the modified immobilized member undergoes a conformational change which changes its affinity to bind to the analyte and consequently, after binding of the analyte, it can be released and after rinsing converted to its original state for reuse. FIGS. 6(a) and (b) illustrate the operational cycle, the difference between these two figures being in that the roles of the analyte and the immobilized member in FIGS. 6(a) and (b) are reversed, i.e. the analyte of FIG. 6(a) is the immobilized member in FIG. 6(b), and vice versa.

FIG. 9 is a schematic representation of an embodiment in accordance with the indirect mode of the invention for the determination of an enzyme capable of breaking the analyte to products which do not bind to the immobilized member. Following reaction of the analyte with the unknown sample, part of the analyte is degraded, depending on the amount of the enzyme in the biological sample and determination of the analyte then allows an indirect determination of the enzyme in the sample.

FIG. 10 illustrates an embodiment in accordance with the indirect mode of the invention similar to the embodiment of FIG. 9, the difference being that the enzyme catabolizes a reaction in which precursor analyte is converted to the analyte which is then determined in a system. Here also, the determination of the analyte allows an indirect determination of the enzyme in the biological sample.

FIG. 12 illustrates an embodiment of the invention wherein the sensitivity is increased by forming a molecular complex on the bond analyte.

FIG. 13 illustrates the manner of modification of a gold electrode as described in Example 1.

FIG. 16 shows the change in maximal current ($\Delta I_{pc}$) at various anti-fluoresein antibody concentrations as described in Example 2.

FIG. 17 shows an antigenic peptide (FIG. 17(a)) which was immobilized onto a gold electrode (FIG. 17(b)) in a manner described in Example 3.

FIG. 23 shows the cathodic current of the α-D-mannopyranoside monolayer electrode illustrated in FIG. 20 in the presence of a constant concentration of Concanavalin A modified by linking thereto a redox molecule in the presence of increasing concentrations of unmodified Concanavalin A.

FIG. 24 shows the amperometric response of electrodes with an immobilized mannose layer, upon exposure to a Concanavalin A solution comprising different concentrations of α-D-mannopyranoside.

FIG. 26(a) are results of an electrode with the DNSP in its original state, whereas

FIG. 27 shows the pick current developed in the electrode of FIG. 25 following incubation with an anti-DNP antibody at two different isomerization states of the immobilized antigen: (b) and (d)—the spiro DNSP configurations (a) and (c)—after photoisomerization to the zwitterionic merocyanine configuration. Isomerization of the spiro state to the merocyanine state and vice versa was induced by light.

FIG. 28 illustrates the manner of modifying the protein Concanavalin A by linking thereto a photoisomerizable group.

DETAILED DESCRIPTION OF THE INVENTION

Figure 7:
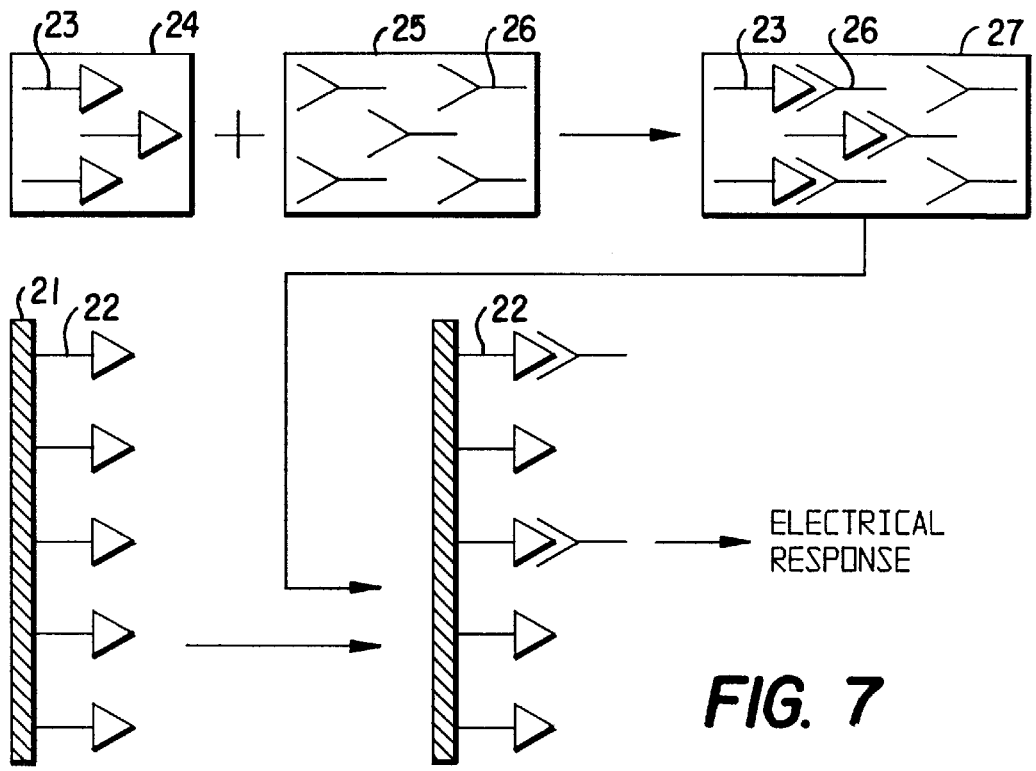
FIG. 7 shows an embodiment in accordance with the indirect mode of the invention for the determination of an agent in a biological sample which is identical to the immoblized member. In this embodiment the unknown sample is first reacted with the analyte and then the determination of the analyte serves as an indirect measure for the agent in the biological sample.

The invention will now be illustrated by several specific embodiments, it being understood that the present invention is not limited thereto. The artisan will no doubt appreciate that the invention can also be carried out by various modifications of its disclosed embodiments as well as by other embodiments and the artisan will have no difficulties of carrying out such other embodiments on the basis of the disclosure in this specification.

Reference is first being made to FIG. 1 which is a schematic representation of an embodiment of the direct mode of the invention. The surface of an electrode 1 is covered by an immobilized layer of a complex comprising a linking group 2 covalently bound to a member of a recognition pair 3. The electrode may typically be made of or coated by gold but may also be made from or coated by other metals such as silver or platinum. The electrode may also be a non metallic electrode, e.g. an ITO electrode. The electrode is immersed in a liquid medium containing a buffer and a redox couple $R^+/R$ 4. Two other electrodes (not shown) are used, a counter electrode typically made of platinum wire or graphite and a reference electrode typically as Ag/AgCl electrodes. The system allows sensitive electrochemical detection of the analyte member 5 of the recognition pair. The electrode immobilized layer is challenged with the analyte member of the recognition pair 5 which binds to its counterpart member immobilized on the surface of the electrode to produce an electrical response. Binding of the analyte member insulates the electrode towards the redox molecules producing a decrease in the electrical response, e.g. cyclic voltammogram. The amount of binding of the analyte member depends on the concentration of the analyte in solution. By measuring the electrical response of the electrode immobilized layer to challenge by various concentrations of analyte for a specified period of time, a calibration curve is obtained which allows an accurate determination of the antibody in a known sample. Concentrations below the nanomolar range are readily detectable. Typical coverage of the electrode surface by the immobilized member where the recognition pair comprises an antigen-antibody is of the order of $10^{-12}$ mole $cm^{-2}$. Binding to 10% or more of the surface is detectable.

The method is also applicable for the analysis of other recognition pairs such as sugar-lectin, ligand-receptor, biotin-avidin, oligonucleotide-DNA, oligonucleotide-protein, oligonucleotide-cell and substrate-enzyme.

The nature of the redox molecules will vary depending on the nature of the recognition pair and whether it is to be bound to a member of the pair. In the simplest system as in FIG. 1, the redox molecules are freely tumbling in solution and are capable of changing their redox state by accepting electrons from or donating electrons to the electrode. An example is ferricyanide/ferrocyanide or the compound having the formula shown in FIG. 18(11).

The linking group is a compound comprising a moiety that facilitates association with, attachment to or chemisorbed onto the electrode surface, typically a sulphur containing moiety for immobilization onto a metallic electrode or an alkoxysaline residue for immobilization onto an ITO electrode; a connecting group; and comprising a functional group which is capable of forming a covalent bond with a moiety of the immobilized member of a recognition pair. An example of a linking group is cystamine. Where members of recognition pairs may be directly immobilized, the linking group is optional.

FIG. 2 shows another embodiment of the direct mode of the invention in which the redox molecule is bound to the analyte. The electrode with the immobilized layer is challenged by a sample containing the analyte member of the recognition pair (step (1)) and subsequently by a solution containing the analyte modified by linking thereto a redox molecule R (step 2).

For testing, the electrode is challenged with the biological or other analyte sample containing an unknown concentration of the analyte, for a fixed time and then thereafter with a solution of the modified analyte. The amount of the modified analyte that binds to the electrode's immobilized layer depends on the amount of unmodified analyte binding. As more immobilized layer sites are occupied by unmodified analyte, less sites will be available to the modified analyte. The electrical response thus inversely correlates with the concentration of the analyte in the tested sample.

The system may be calibrated by challenging the electrode with different known concentrations of the analyte and subsequently with a fixed concentration of modified analyte and then measuring the electrical response.

Reference is now being made to FIG. 3. The embodiment shown schematically in this figure is very similar to that shown in FIG. 2 with the difference being that the electrode in this embodiment is challenged simultaneously with the sample containing an unknown analyte concentration and with the modified analyte. The resulting electrical response is qualitatively similar.

As will no doubt be appreciated, the embodiments shown above are interchangeable in that the analyte in one embodiment may be the immobilized member in another and vice versa. For example, in order to detect the presence of a certain antigen in a sample, the immobilized member may be an antibody specifically directed against this antigen, whereas in order to detect the presence of the antibody, the immobilized member will be the antigen. This is illustrated in FIGS. 4 and 5 which are essentially identical to FIGS. 2 and 3 with the roles of the analyte and immobilized member reversed.

Reference is now being made to FIG. 6 which is a schematic representation of another embodiment in accordance with the direct mode of the invention. This embodiment allows the regeneration of the electrode after performance of a measurement to allow reuse in a subsequent measurement. This feat is achieved in accordance with this embodiment, by modifying the immobilized member 11 by a group 12, which as shown in FIG. 6(c) has two isomerization states, A and B, and is capable of switching reversibly between the two states by exposure to light at energies $hv_1$ (having a wavelength $\lambda_1$) and of energy $hv_2$(having a wavelength $\lambda_2$). The switching between the two isomerization states A and B causes a confirmational change of the modified immobilized member which brings to a change in its affinity to binding to analyte 13: in state A, the modified immobilized member is capable of binding analyte 13 with a high affinity; in state B, the affinity of binding to the analyte becomes very low.

FIGS. 6(a) and (b) are very similar, the difference being in that the role of the immobilized member 11 and ligand 13 of FIG. 6(a) have been reversed in that analyte 13 and immobilized member 11 of FIG. 6(a) are immobilized member 11' and analyte 13', respectively. Apart from that the embodiments are identical and accordingly the description below will relate only to FIG. 6(a), it being understood that it applies equally also to the embodiments shown in FIG. 6(b), and thus the stages in the use cycles $a_1$, $a_2$, $a_3$, $a_4$ and $a_5$ correspond to stages by, $b_1$, $b_2$, $b_3$, $b_4$ and $b_5$, respectively of FIG. 6(b).

In the initial stage $a_1$, group 12 is in an isomerization state A where it has high affinity of binding to analyte 13. In the presence of analyte 13, the analyte binds to the immobilized member, stage $a_1$, which binding gives rise to a change in the electrochemical response, $a_3$. After performance of the measurement, the electrode is iluminated by a light of a wavelength $\lambda_1$, and consequently group 12 assumes its isomerization state B and consequently there results a confirmational change of immobilized member 11 giving rise to a low affinity of binding to analyte 13. Consequently, as in stage $a_4$, the anlayte 13 dissociates from immobilized member 11. The system is then rinsed to remove the unbound analyte, and after removal, stage $a_5$, the electrode is illuminated with light of a wave-length $\lambda_2$, and consequently group 12 is isomerized back to its state A and the modified immobilized member assumes its original conformation, $a_1$. At this stage $a_1$, the electrode is ready for reuse.

It will be appreciated that similarly as in the embodiment of FIG. 5, also in the embodiment of FIG. 6, use can also be made with a modified analyte shown in FIGS. 2 and 3.

Reference is now being made to FIG. 7 showing an embodiment in accordance with the indirect mode of the invention. In this embodiment, a system comprising an electrode 21 with a layer of immobilized members 22 is used for determination of an agent 23 in a biological sample 24, which agent is identical (albeit not immobilized) to the immobilized member. In accordance with this embodiment, a solution 25 comprising a known concentration of an analyte 26 is reacted with sample 24. Following this reaction there is binding between analyte molecules 26 and agent molecules 23, the degree of binding depending on the agent's concentration. The electrode is then challenged with the reacted solution 27 following which there is binding of free analyte molecules to the immobilized member, the degree of binding depending on the amount of free analyte molecules in solution 27. The change in the electrical response allows determination of the concentration of the free analyte 26 in solution 27 which in turn serves determination of the agent 23 in sample 24.

Figure 8:
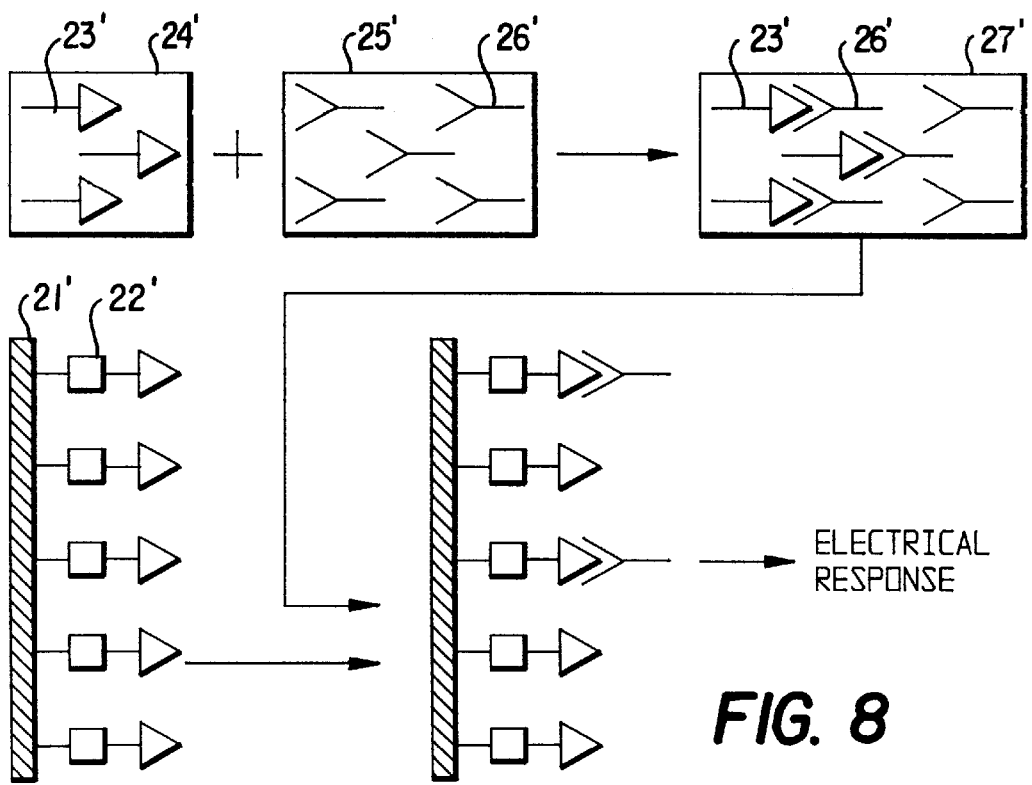
FIG. 8 is a schematic representation of an embodiment in accordance with the indirect mode of the invention, similar to that of FIG. 7 with the difference being that in this case the tested agent is not identical to the immobilized member but has similar binding affinity to the analyte as the immobilized member.

Reference is now being made to FIG. 8 showing another embodiment in accordance with the indirect mode of the invention. The embodiment of FIG. 8 is in essence similar to that of FIG. 7 with the difference being that immobilized member 22' is not identical to agent 23' to be determined in sample 24' but rather has only similar binding characteristics to analyte 26'.

Reference is now being made to FIG. 9 showing a further embodiment in accordance with the indirect mode of the invention. This embodiment allows determination of an enzyme 31 which as shown in FIG. 9(a) catalyzes a reaction in which an analyte 32 is broken down to products 33 and 34.

As shown in FIG. 9(b), a solution 35 containing a known concentration of analyte 32 is reacted with a biological sample 36 containing an unknown concentration of enzyme 31, which is the agent to be determined in this biological sample. Following this reaction, some of the analyte 32 is degraded by the enzyme to reaction product 33, the degree of degradation depending on the concentration of enzyme 31 in sample 36. Electrode 37, carrying a layer of immobilized members 38 is then reacted with reacted solution 39, whereupon free analytes 32 bind to the immobilized members 38 on the electrode. The change in the electrical response allows the determination of the analyte in solution 39 which in turn allows the determination of enzyme 31 in sample 36.

Reference is now being made to FIG. 10 which is similar to the embodiment of FIG. 9 and accordingly like components have been given like numbers with a prime indication. In this embodiment, enzyme 31' bring to reaction in which precursor analyte molecules 33' and 34' are catabolized to yield analyte molecule 32'. In this embodiment as shown in FIG. 10(b), a solution 35' containing a known concentration of precursor analyte 33' is reacted with a sample 36' containing an unknown amount of enzyme 31'. Electrode 37' having immobilized thereon a layer of member 38', is then challenged with reacted solution 39', whereupon analyte molecules 32' bind to the immobilized member 38', the degree of binding depending on the level of analyte molecules in solution 39'. By determining a change in the electrical response, the concentration of analyte 32' in solution 39' is determined, which allows in turn determination of enzyme 31' in sample 36'.

Figure 11:
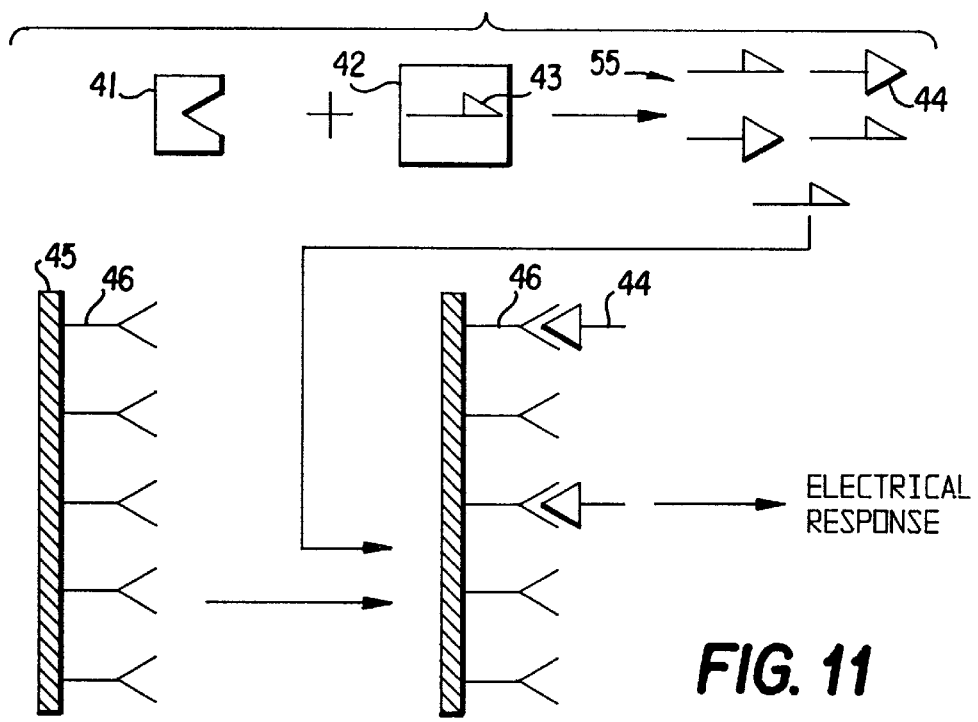
FIG. 11 illustrates a further embodiment of the indirect mode of the invention in which the analyte is a product of an enzymatic reaction in which a precursor analyte present in a biological sample is converted by an enzyme to the analyte which is then determined in a system; the determination of the analyte provides an indirect measure of the precursor analyte, which is the tested agent in the biological sample.

Reference is now being made to FIG. 11 illustrating a still further embodiment of the indirect mode of the invention. In this embodiment, an unknown amount of an enzyme 41, which catabolizes a reaction similar to that of enzyme 31' in the embodiment of FIG. 10, is added to sample 42 which contains an unknown amount of biological agent 43 to be determined. This agent is in fact a precursor analyte which is converted by enzyme 41 to analyte 44. Following the reaction, electrode 45 having immobilized thereon a layer of an immobilized member 46 is reacted with solution 55 following which there is binding of analyte molecules 44 to the immobilized member 46, the degree of binding being dependent on the concentration of analyte 44 in solution 55. The change in the electrical response which is determined, serves then as a measure for the determination of the concentration of analyte 44 in solution 55, which in turn serves to determine the concentration of agent 43 in biological sample 42.

Reference is now being made to FIG. 12 showing an embodiment in accordance with the invention in which the change in electrical response of the electrode resulting from binding of the analyte to the bound member is amplified by the use of agents which bind to the bound analyte. In FIG. 13(a) there is seen an electrode 51 carrying an immobilized member 52, which in this case is an antigen which binds specifically to an antibody 53. A cyclic voltammogram of this electrode yields a control response 54. When the electrode is challenged with a solution comprising antibody 53, there is binding of the antibodies to the electrode as seen in FIG. 13(b). Cyclic voltammogram 54' shows a decrease in the electric response. Where, however, there is only a minute quantity of antibody 53 in the tested sample, the change in this response relative to control 54 is small.

In order to amplify the change in electrical response, the electrode is then challenged with a solution comprising an anti-antibody 55 which binds specifically to antibody 53. As a result, there is the formation of a molecular complex 56 on the bound antibody which hinders further the access of the redox couple $R^+/R$ to the surface of the electro material of the electrode and consequently, a cyclic voltammogram 54" shows a marked decrease when compared to the control 54.

The invention will now be illustrated further by the Examples below.

EXAMPLE 1

Antigen-Antibody Recognition Pair (direct mode) Determination of the anti-DNP-antibody by an electrode with an immobilized layer comprising DNP The manner of construction of the electrode used in this example is shown in FIG. 13. A polished gold electrode (area $3 \times 10^{-2}$ cm$^2$) was immersed in a solution of 3,3'-dithiodipropionic acid bis(N-hydroxy-succinimide ester) 0.1M in dry DMF, for 2 hours. The electrode was washed with dry DMF and then immersed in 0.025M solution of Nε-2,4-DNP-lysine in DMSO:THF (1:1) and 15 μL (per 5 cc) diethylpropyl amine overnight at room temperature.

The electrochemical experiments were performed in a three electrode cell using the Nε-2,4-DNP-lysine antigen monolayer electrode as a working electrode, a Pt-wire as a counter electrode and Ag/AgCl as the reference electrode. The electrolyte was composed of 1.1 mM $K_4Fe(CN)_6$ being the redox molecule, and 0.15M NaCl in phosphate buffer solution (0.01M, pH–7.4). The temperature was 37±2° C. and the scan rate was 200 mV/sec. The electrode was immersed for 15 min. in a solution of antibody anti-DNP. The amperometric responses of the $K_4Fe(CN)_6$ (the redox probe) at different antibody anti-DNP concentrations were recorded.

Figure 14A:
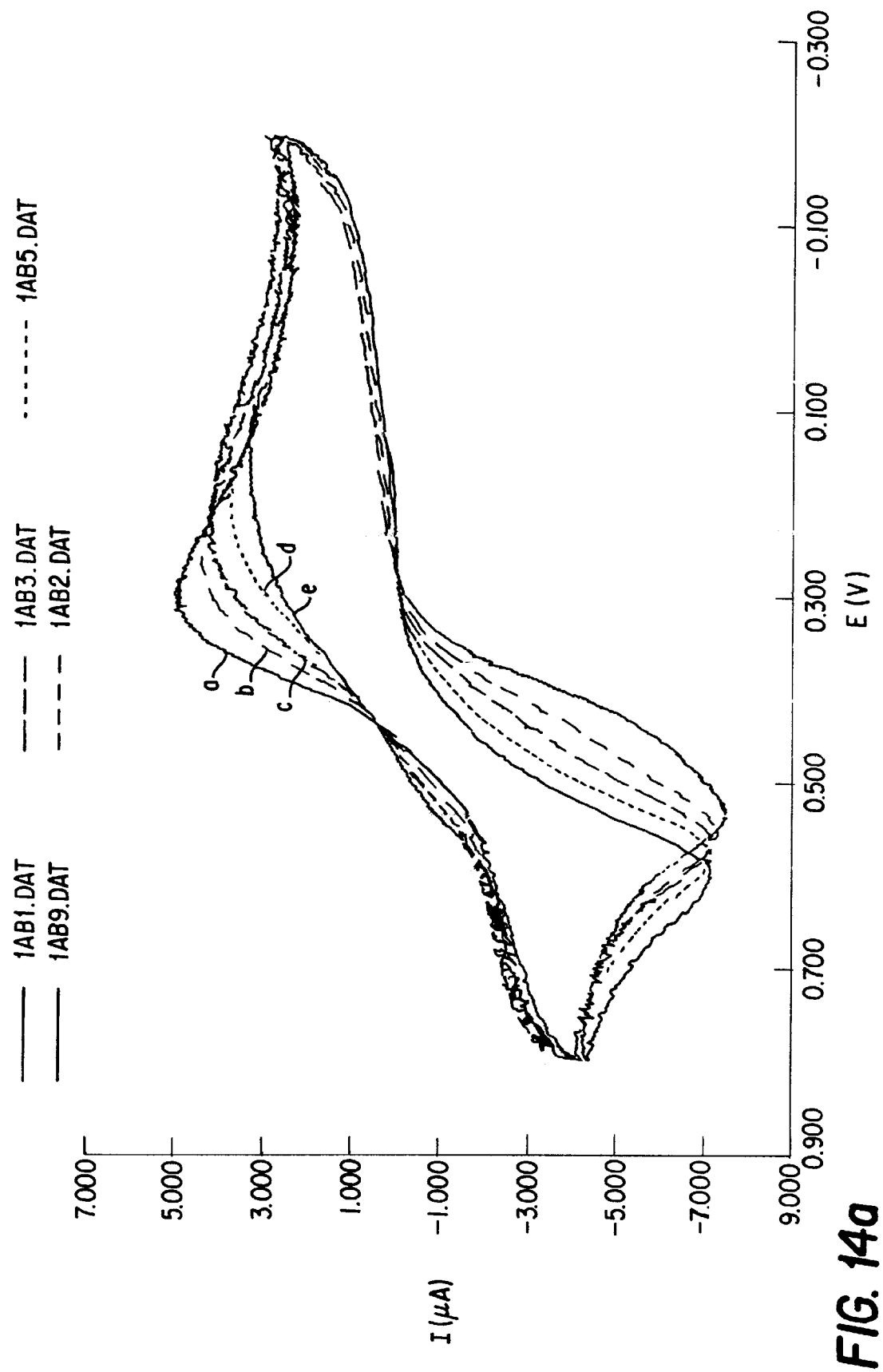
FIG. 14(a) shows a cyclic voltammogram respnose of the DNP electrode of Example 1 in the absence (curve a) of and at different concentrations of an anti-DNP antibody (curves b–e).
Figure 14B:
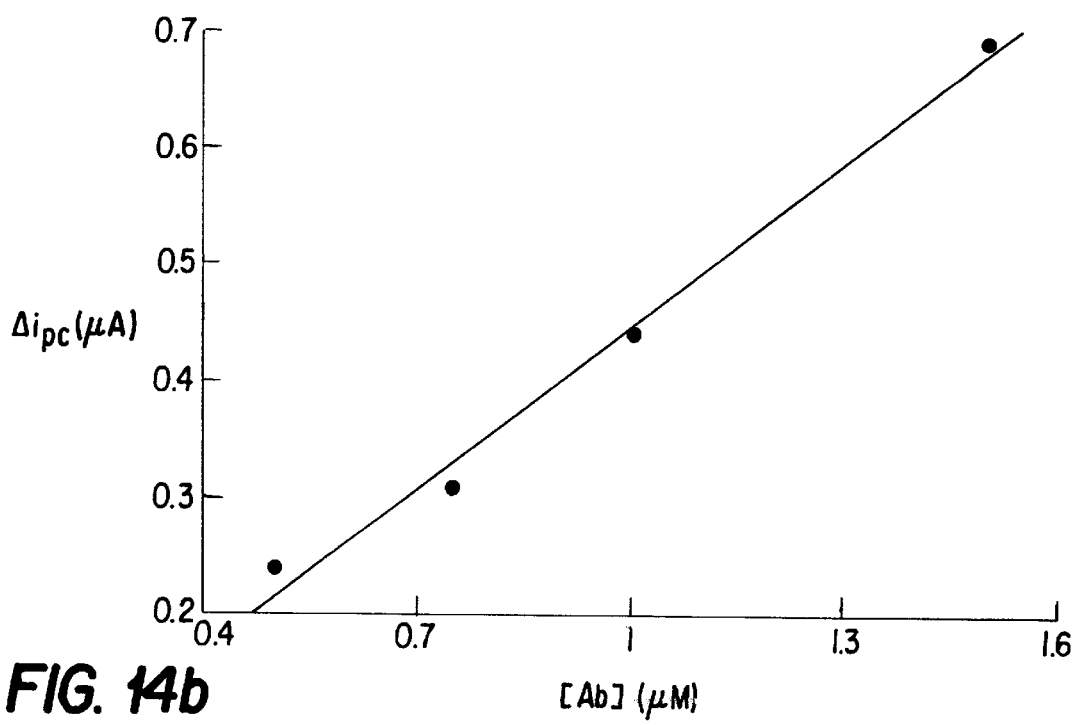
FIG. 14(b) shows the change in the current response at the peak ($\Delta I_{pc}$), at various antibody concentrations versus control (without antibody).

The cyclic voltammograms without anti-DNP antibody (control-curved marked a) and with increasing concentrations of anti-DNP antibody (curves marked b-e), are shown in FIG. 14(a). As can be seen, there is a decrease in the electrical response as a function of antibody concentration. FIG. 14(b) shows the change in the current response at the peak versus control ($\Delta I_{pc}$) as a function of the antibody concentration. As can be seen, the change in the amperomentric response is a linear function of the antibody concentration. As can be seen further, antibody concentrations as low as 0.5 μM can be detected.

EXAMPLE 2

Figure 15:
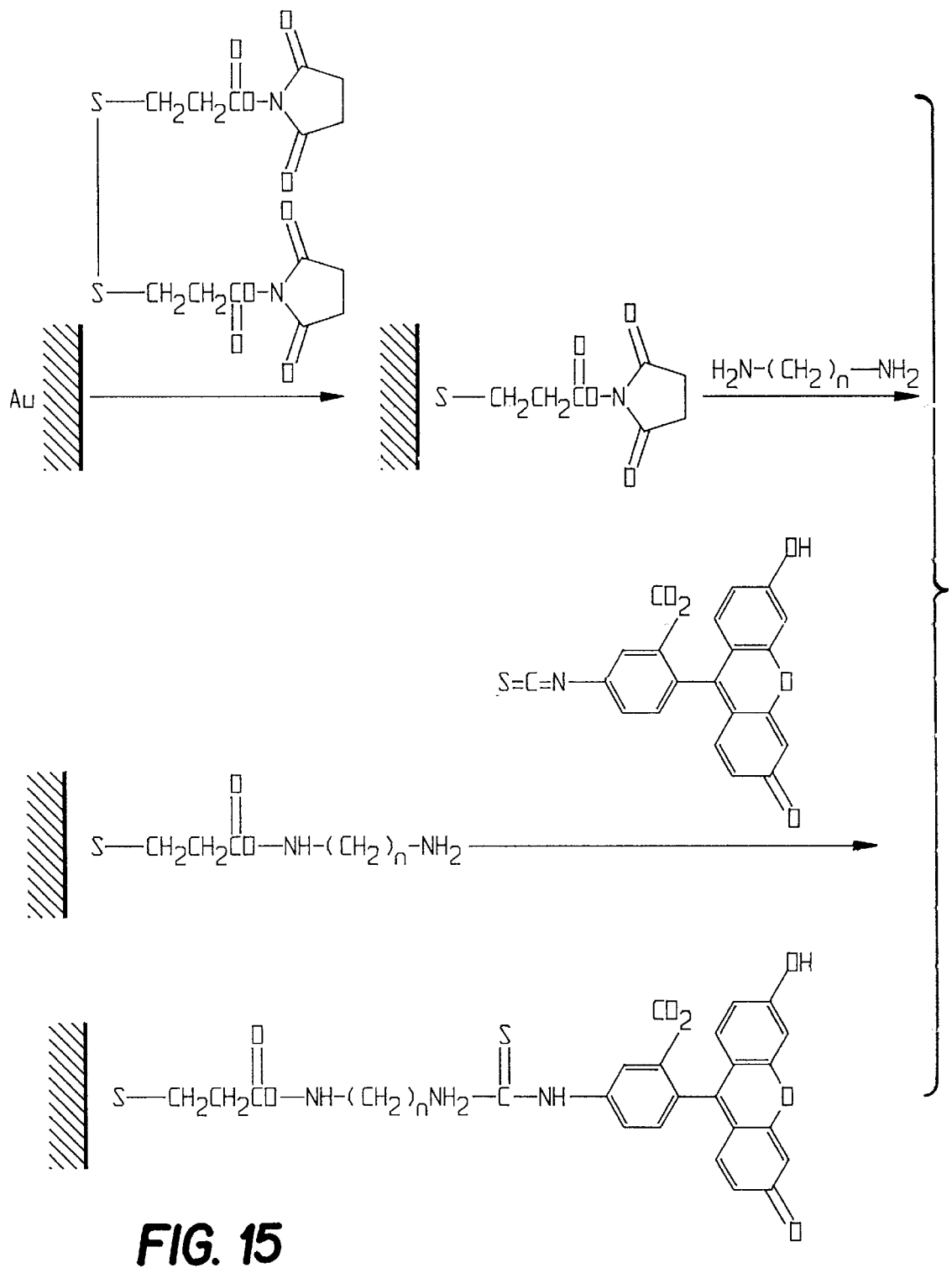
FIG. 15 illustrates the manner of immobilization of a fluorescein monolayer on a gold electrode as described in Example 2.

Antigen-Antibody Recognition Pair (direct mode)
Determination of anti-fluorescein-antibody by an electrode with an immobilized fluorescein layer The manner of preparation of an electrode used in this Example is shown in FIG. 15. A polished gold electrode (area 3.·0$^{-2}$ cm$^2$) was immersed in a solution of 3,3'-dithiodipropionic acid bis(N-hydroxy-succinimide ester) 0.02M in DMSO for 2 hours. The electrode was washed with DMSO and with THF and then immersed in a solution that contains 1,12-diaminododecane, 25 mg in 2.5 ml THF for 24 hours at room temperature.

The modified electrode was immersed for another 24 hours at room temperature in a solution of 20 mg fluorescein isothiocyanate solubilized in 300 μl of dry DMF.

The electrochemical experiments were performed in a three electrode cell using the fluoresein antigen monolayer electrode as the working electrode, a Pt-wire as a counter electrode and Ag/AgCl as the reference electrode. The electrolyte was composed of 1.1 mM K$_4$Fe(CN)$_6$, being the redox molecule and 0.15M NaCl in phosphate buffer solution (0.01M, pH=7.4). The temperature was 37±1° C. and the scan rate was 200 mv/sec.

FIG. 16 shows the amperometric response of the fluorescein electrode as a function of anti-fluorescein antibody concentration. The amperometric response was measured after 1 min. of incubation of the electrode in the antibody solution. As can be seen there is a linear dependency between the antibody concentration and the change in the amperometric response.

EXAMPLE 3
Antigen-Antibody Recognition Pair (direct mode) Determination of an anti-peptidic antibody by the use of an electrode with an immobilized peptidic layer An antigen peptide shown in FIG. 17(a) was synthesized by the F-MOC solid phase peptide synthesis method using protected Cys, Asp, Tyr, Lys side chains that are acid labile but stable under basic (piperidine) conditions, used for F-MOC removal (G. G. Fields et al., *Int. J. Peptide Protein Res.*, 33, 1989, 298–303). The crude peptide was purified by HPLC (RP-18).

An immobilized layer antigen electrode, shown schematically in FIG. 17(b) was prepared by immersing a polished gold electrode (area 3×10$^{-2}$ cm$^2$) into 300 μl of 0.1M peptide solution of (2:1) H$_2$O:CH$_3$CN, 0.1% TFA, pH=1, for a period of three hours.

Figure 18:
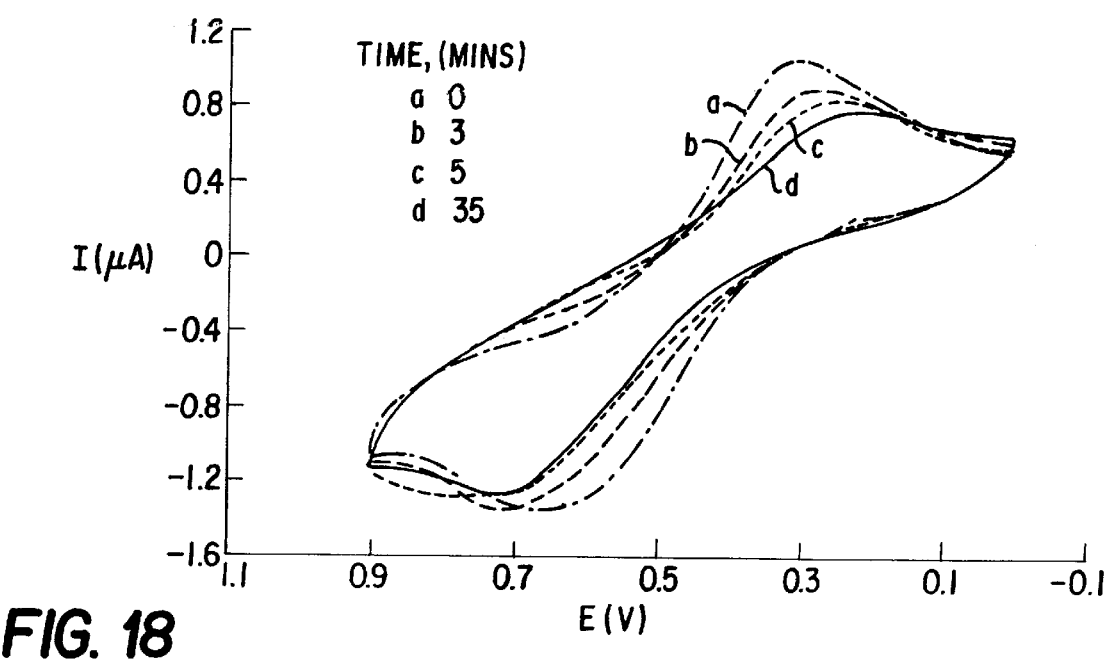
FIG. 18 shows cyclic voltammograms of a gold electrode modified with the antigenic peptide of FIG. 17, at times equal 0 (curve A), after 3 min. (curve B), after 5 min. (curve C) and after 35 mins. (curve D) following addition of an anti-peptide antibody.

Electrochemical measurements were performed in a three-electrode cell using the modified electrode (FIG. 17(b)) as working electrode, a Pt wire as counter electrode, and Ag/AgCl as reference electrode. The electrolyte compositions were 1.1 mM K$_4$Fe(CN)$_6$, 0.15M CaCl$_2$ in phosphate buffer solution 0.01M, (pH=7). The temperature was 20±1° C. and the scan rate was 200 mV/sec. The redox molecules ferricyanide/ferrocyanide accept electrons from or donate them to the electrode and their increasing insulation from the electrode functions as a measure to determine the association of the antibody to the antigen immobilized layer electrode. FIG. 18 shows the cyclic voltamograms of the electrical response of the antigen immobilized layer electrode in the presence of the redox molecule. Upon addition of the antibody at a concentration of 0.23 μg/ml, a gradual decrease in the electrochemical response is seen (curves b to d). After 35 minutes (in curve d) the cathodic decrease corresponds to 55% of its original value in the absence of antibody.

EXAMPLE 4
Sugar-Lectin Recognition Pair (direct mode) Determination of Conconavalin A (Con A) by the use of an electrode having an immobilized sugar layer The protein Con A is a lectin which binds specifically to the monosaccharide α-D-Mannopyranose. Con. A was modified by linking to it the redox molecule N-methyl-N'-carboxymethylene-4,4'-bipyridinium having the formula (11) in FIG. 19.

The chemical attachment of N-methyl-N'-carboxymethylene-4,4'-bipyridinium to Con A was performed by means of carbodiimide coupling of the carboxy group to amino group of the lysine residues of the protein molecule. 23 mg of N-methyl-N'-carboxymethylene-4,4'-bipyridinium, 80 mg HEPES and 184 mg of urea were solubilized in 1.6 ml of distilled water, the pH of the solution was adjusted to 7.2 and then cooled to 4° C. 50 mg. of Con. A in 1 aqueous solution (4° C.) was added to the solution and then 5.5 mg of N-hydroxy-sulfosuccinimide sodium salt (sulfo-NHS) and 12 mg 1-ethyl-3-(3-dimethylaminopropyl) carbodiimide (EDC) as coupling reanalytes were added. The resulting mixture was allowed to react overnight (4° C.). The resulting solution was dialyzed against phosphate buffer pH=7 (0.0875M, MnCl$_2$ 0.1 mM, CaCl$_2$ 0.1 mM, NaCl 0.15M) and then against distilled water. The dialyzed solution was centrifuged (30 min, 4° C., 15000 rpm), and the supernatant was lyophilized to obtain a powder of the chemically modified Con. A (30 mg). The loading of concanavalin A by N-methyl-N'-carboxymethylene-4,4'-bipyridinium corresponds to 3 bipyridinium groups per protein molecule.

Figure 20:
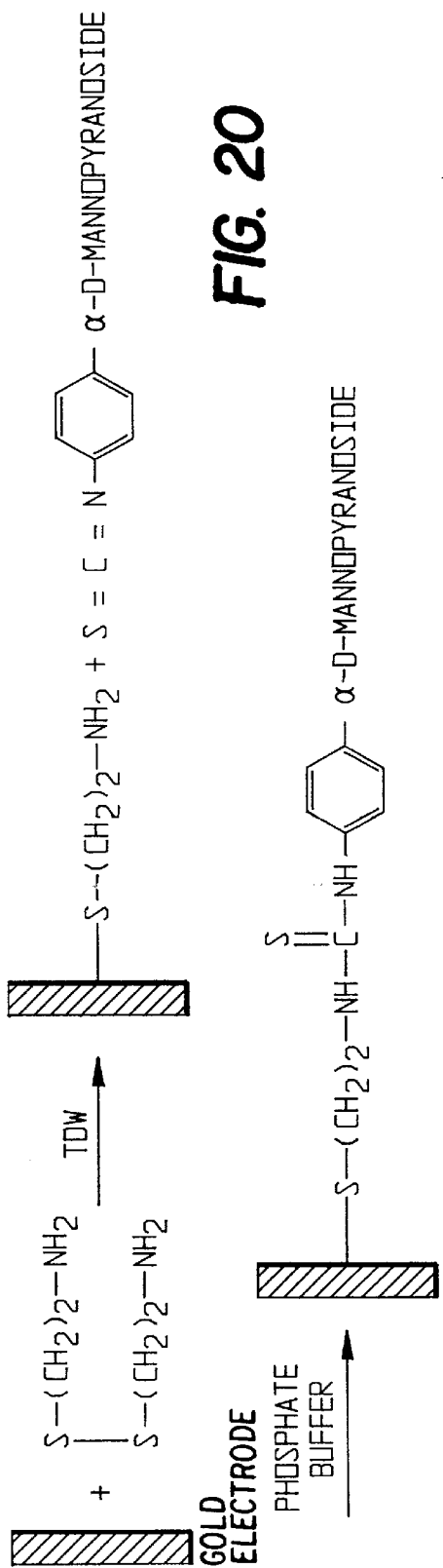
FIG. 20 illustrates the procedure of immobilization of a monosaccharide α-D-Mannopyranose layer on the surface of a gold electrode as described in Example 4.

The monosaccharide immobilized layer associated with the Au electrode was prepared by the sequence of transformations illustrated in FIG. 20. A polished gold electrode (area –3×10$^2$cm$^{-2}$) was treated with 0.02M aqueous solution of cystamine for two hours. The resulting cystamine modified electrode was then reacted with the functionalized monosaccharide, p-isothiocyanatophenyl α-D-mannopyranoside (formula (12) in FIG. 21) by immersing the electrode immobilized layer in a solution of 1 mg of p-isothiocyanatophenyl α-D-mannopyranoside in 300 μL of phosphate buffer 0.1M, pH=7.3, to yield the thiourea-linked monosaccharide immobilized layer electrode.

The electrochemical experiments were performed in a three electrode cell using the monosaccharide immobilized layer electrode as working electrode, a Pt-wire as counter electrode, and Ag/AgCl as reference electrode. The electrolyte was 1 mM KCl in phosphate buffer, 0.1M (pH=8), the temperature was 20±1° C., and the scan rate was 1000 mv/sec.

Different concentrations of Con. A and a constant concentration of Con. A modified by linking to it redox molecules (modified Con A) were introduced into the cell. The systems were allowed to equilibrate for 2 hours and the cyclic voltammograms were recorded.

Figure 21:
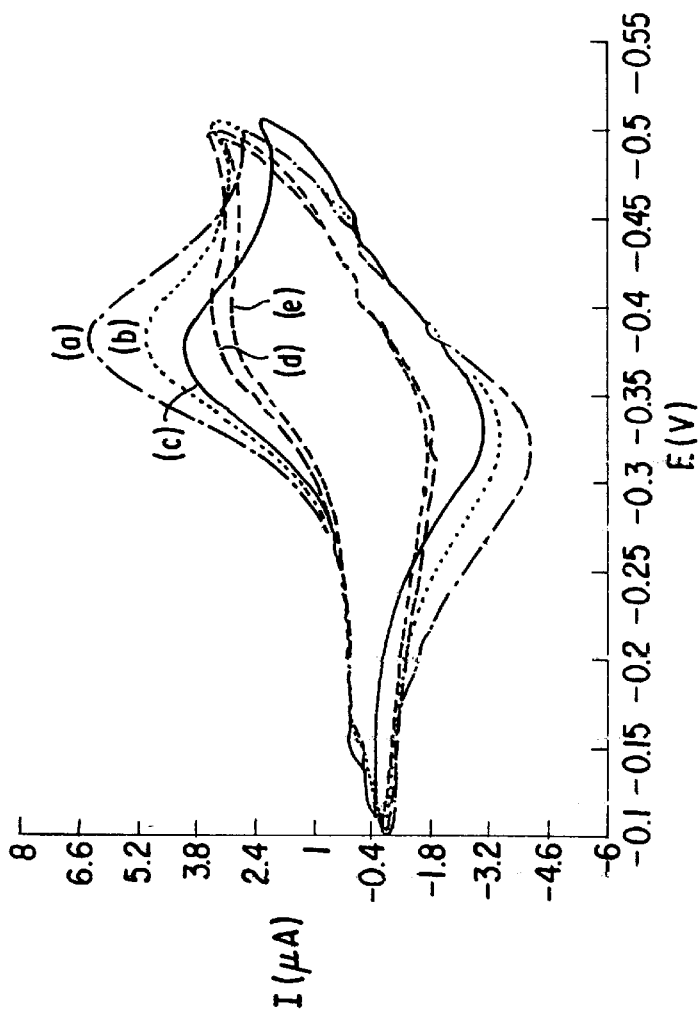
FIG. 21 shows cyclic voltammograms of a gold electrode modified with an α-D-mannopyranoside monosaccharide layer, as illustrated in FIG. 19, following challenging of the electrode with different concentrations of Concanavalin A in the presence of constant concentration of 25 μM of Concanavalin A modified by linking thereto a redox molecule being N-methyl-N'-carboxymethylene-4,4'-bipyridinium. The concentrations of unmodified Concanavalin A were 0 (curve a), 2.5 μM (curve b), 5 μM (curve c), 10 μM (curve d) and 20 μM (curve e).

FIG. 21 shows the electrochemical responses of the system at different Con. A concentrations and constant concentration of modified Con. A (25 μM). Curve (a) is the electrochemical response when the concentration of Con. A is 0M and the cathodic current is high, and where the concentrations of Con. A are (b) 2.5 μM; (c) 5 μM; (d) 10 μM, (e) 20 μM. As the concentration of Concanavalin A increases, the cathodic current decreases.

Figure 22:
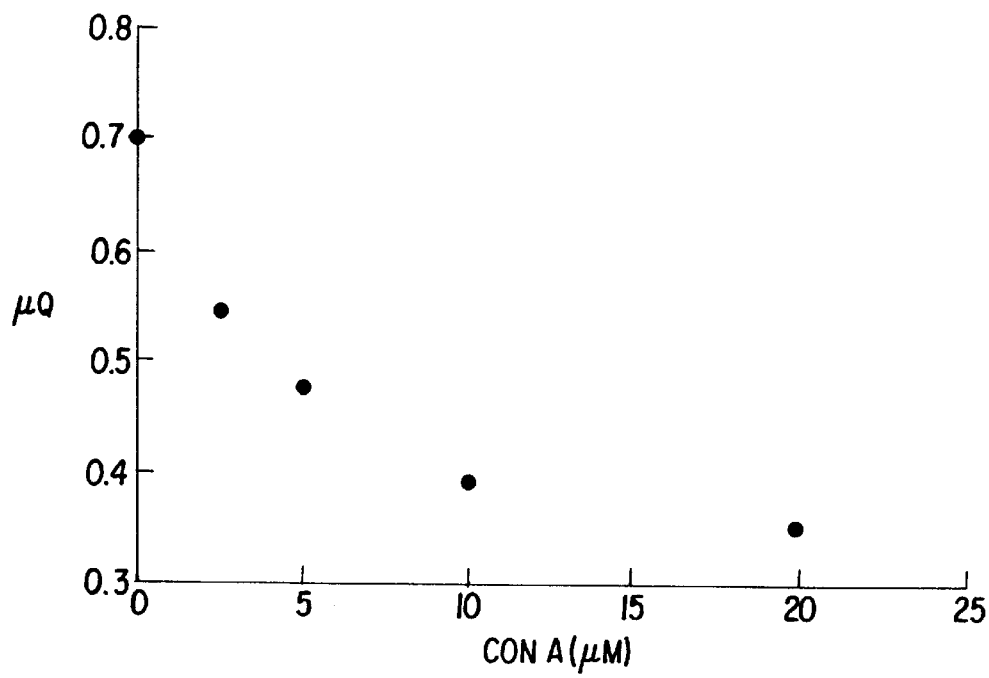
FIG. 22 shows a calibration curve of the decrease in charge transfer as a function of unmodified Concanavalin A concentration in the system of FIG. 20.

FIG. 22 shows the calibration curve of the charge involved with the reduction of modified Con. A vs. the concentration of unmodified Con. A. This change represents the integrated areas of the reduction or oxidation curves of the voltammograms shown in FIG. 23. By using this calibration curve unknown concentrations of Con. A can be determined down to a level of 1×10$^{-6}$M.

FIG. 23 shows the cathodic current involved at the reduction of the modified Con. A as a function of unmodified Concanavalin A.

EXAMPLE 5
Sugar Lectin Recognition Pair (indirect mode)
Determination of Con A by the use of an electrode having an immobilized sugar layer A polished gold electrode (area $3 \times 10^{-2}$ cm$^2$) was immersed in an aqueous solution of 0.02M cystamine for 2 hours. The electrode was washed with H$_2$O then immersed in a solution of 1.5 mg α-D-mannopyranosylphenylisothiocyanate solubilized in 0.125 ml DMSO and 0.95 ml 0.1M potassium phosphate buffer, pH=7, at room temperature.

A solution composed of 1 potassium phosphate buffer, pH=7.8, 1 mM KCl, 0.1 mM MnCl$_2$, 0.1 mM CaCl$_2$, $1 \times 10^{-7}$M Con. A was mixed with a solution composed of $1 \times 10^{-4}$M, $1 \times 10^{-5}$M, $1 \times 10^{-6}$M, $1 \times 10^{-7}$M, and $1 \times 10^{-8}$M of α-D-mannopyranoside. The mixture was incubated for 30 min. at room temperature and a modified electrode was then immersed in this mixture for 6 min. The electrodes were then washed with the same buffer as above and used for electrochemical measurements.

The electrochemical experiments were performed in a three electrode cell using the mannopyranoside monolayer electrode as the working electrode, a Pt-wire as a counter electrode and Ag/AgCl as the reference electrode. The electrolyte was composed of 1 mM K$_4$Fe(CN)$_6$ being the redox probing molecule and 1 mM KCl in phosphate buffer solution (0.1M, pH=7.8). The scan rate was 200 mV/s.

FIG. 24 shows the amperometric responses of electrodes with an immobilized mannose layer upon interaction with the above Con A solutions that include different concentrations of α-D-mannopyranoside. This curve may serve as a calibration curve for analysis of mannose in an unknown sample by such electrodes.

Figure 19A:
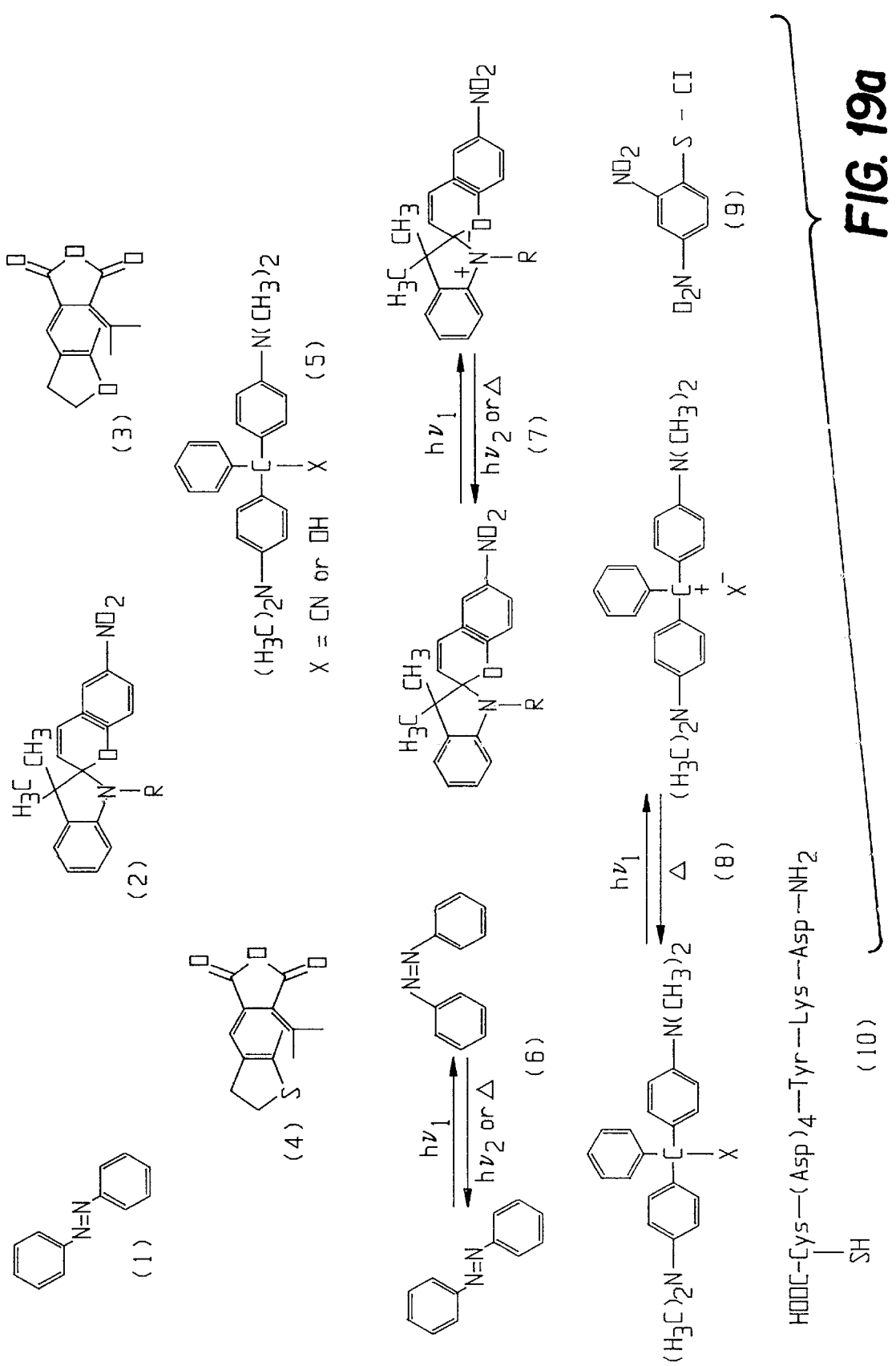
FIG. 19 shows the formula of the compounds 1–17 referred to in the text.

EXAMPLE 6
Reversible binding of Antigen-Antibody Recognition Pair (direct mode)
Determination of an anti-DNP antibody by an electrode with an immobilized dinitrospiropyran (DNSP) pair The affinity of anti-DNP is high towards the isomer dinitrospiropyran (formula 13 (a) in FIG. 19) but low towards the isomer dinitromerocyanine (formula 13(b) in FIG. 19).

The dinitro spiropyran compound and its derivatives exhibit reversible photoisomerizable properties. Illumination of dinitrospiropyran (formula 13 (a)) in a wavelength between 300 nm and 400 nm, isomerizes this compound to dinitromerocyanine (formula 13(b)) while irradiation of dinitromerocyanine in the visible spectral region of more than 480 nm results in isomerization to yield dinitrospiropran.

An electrode with an immobilized layer of dinitrospiropyran (DNSP) was constructed according to the Scheme illustrated in FIG. 24. A polished gold electrode (area $3 \times 10^{-2}$ cm$^2$) was immersed in a 0.2M cystamine dihydrochloride aqueous solution for two hours. The cystamine modified electrode was washed with dry DMF and then immersed into 0.2M of the spiropyran functionalized active ester having the formula 14(a) in FIGS. 19 and 25 in dry DMF solution. The resulting electrode was rinsed with distilled water.

The DNSP antigen immobilized layer electrode was examined both as an electrical immunosensor for anti-DNP-antibody and for reversible detachment of the antibody. The DNSP electrode in its first state ((a) in FIG. 25) was challenged by anti-DNP-antibody so as to form antigen-antibody pair complexes and then treated for reuse by consecutive irradiation at between 400 nm and 300 nm for conversion of the antigen to its second state ((b) in FIG. 25) and release of antibody and subsequent irradiation at above 480 nm (or thermal treatment) to restore the immobilized antigen layer to its first, active state.

The electrochemical measurements were performed in a three electrode cell using the DNSP antigen immobilized layer electrode as working electrode, a Pt-wire as counter electrode and Ag/AgCl electrode as reference electrode. The electrolyte was composed of 1 mM K$_4$Fe(CN)$_6$, 0.15M NaCl, in phosphate buffer solution (0.01M, pH=7.4) and 8 μM of anti-DNP, the temperature was 37±1° C. and the scan rate was 200 mV/sec.

Figure 25:
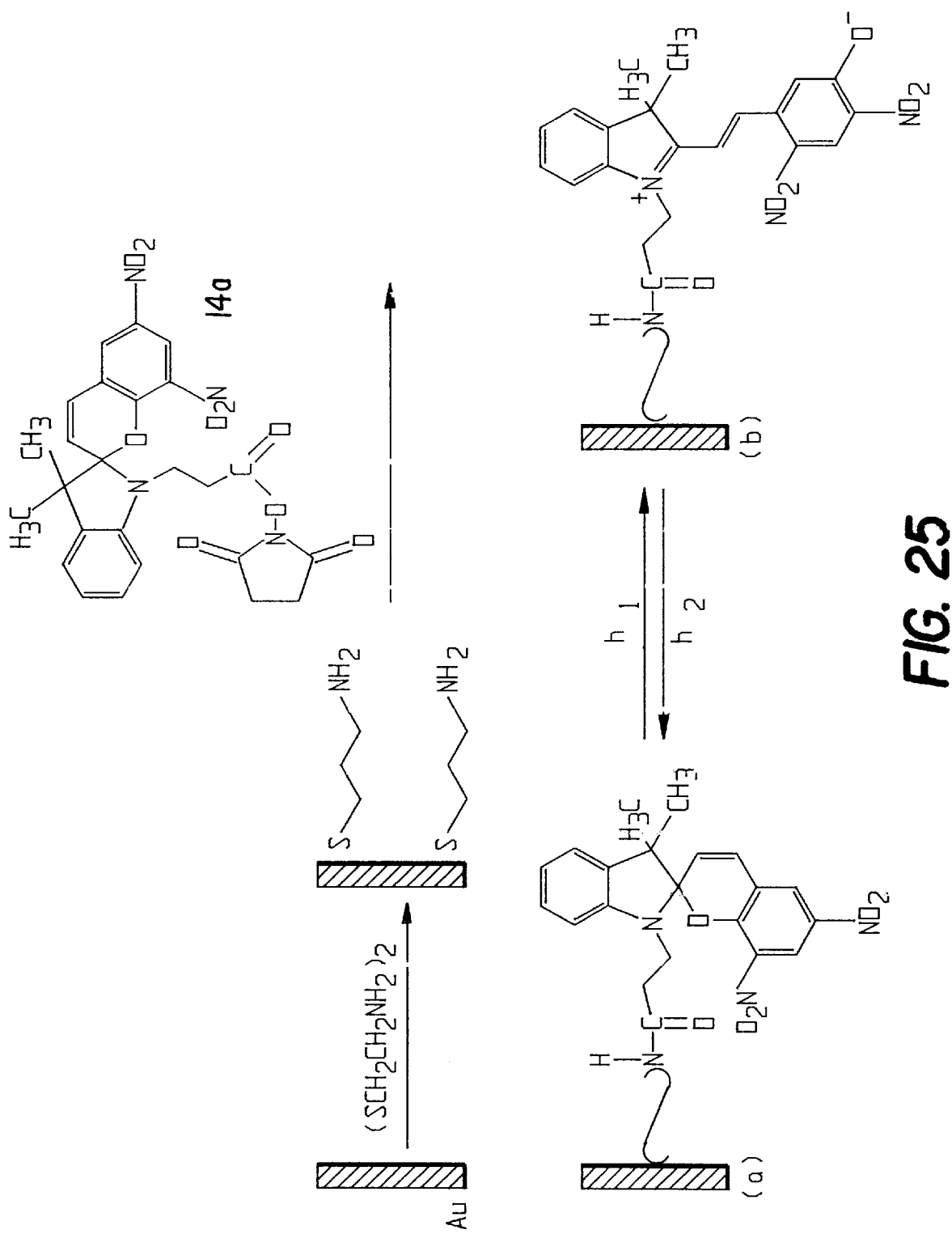
FIG. 25 illustrates the immobilization of a dinitrospiropryan (DNSP) monolayer on a gold electrode as described in Example 6.
Figure 26A:
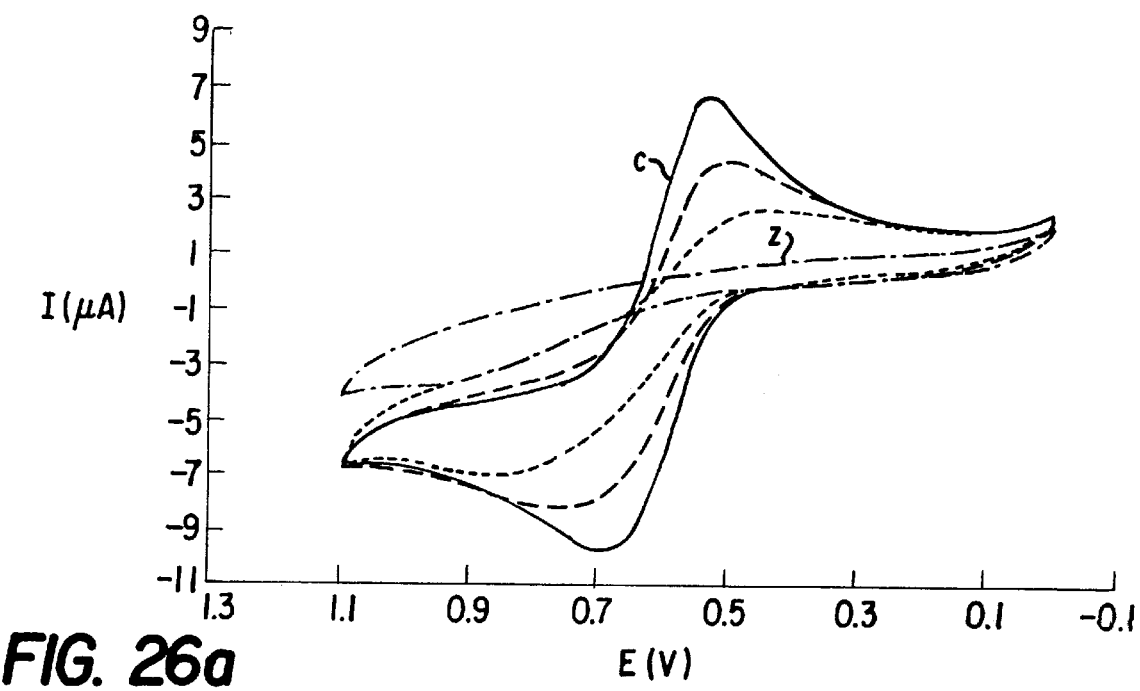
FIG. 26(a) shows cyclic voltammograms of an electrode having an immobilized layer of DNSP following 16 mins. incubation with anti-DNP antibody.
Figure 26B:
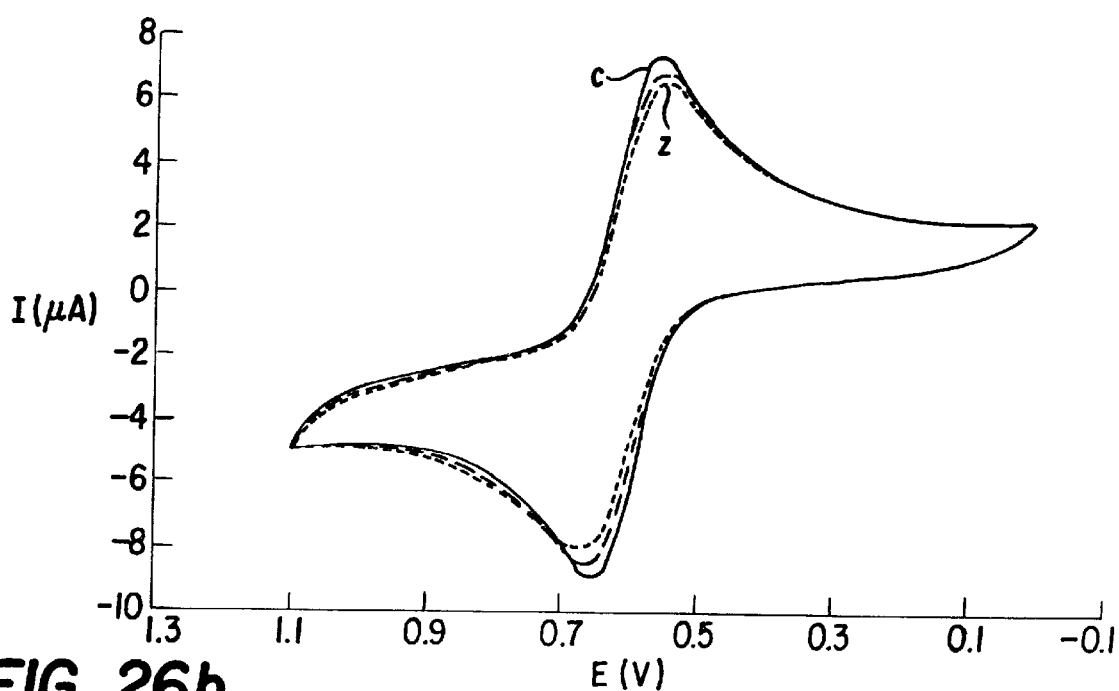
FIG. 26(b) is the same electrode after photoisomerization of the DNSP to the zwitterionic merocyanine configuration.
Figure 29:
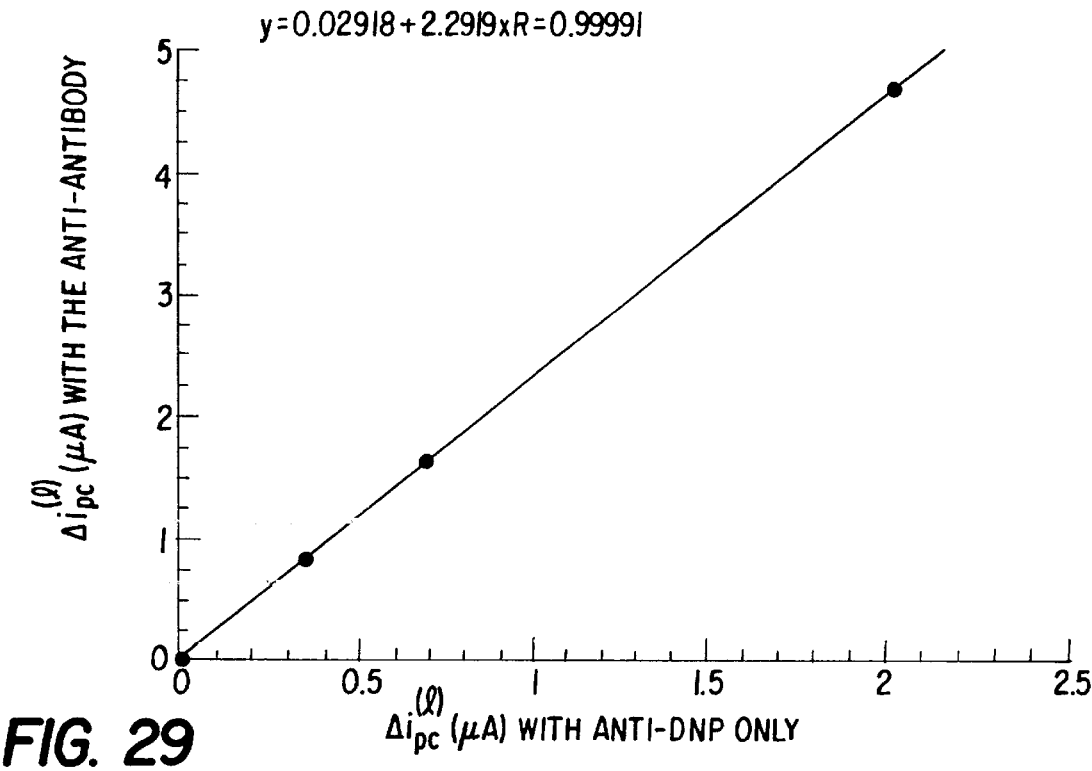
FIG. 29 depicts the change in response following challenge of an electrode with immobilized DNSP with an an-i-DNP-antibody ($\Delta i^{(1)}_{pc}$) versus the change in electrical response following further challenge of the electrode which an anti-antibody against anti-DNP-antibody.
Figure 30A:
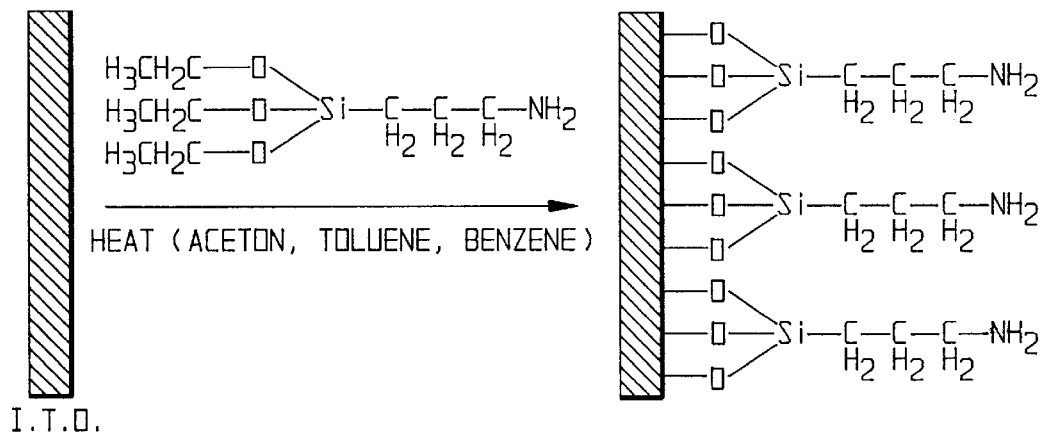
FIG. 30 illustrates the procedure of modification of an indium tin oxide (ITO) electrode, which is a transparent glass electrode, by immobilizing thereon a linking group being 3-amino propyltriethoxysaline.
Figure 30B:
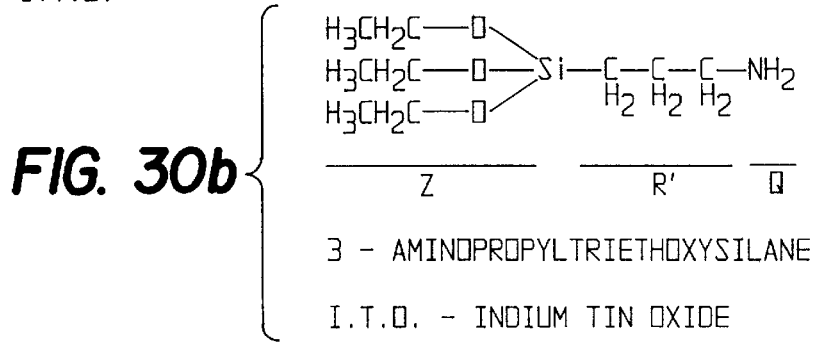

Reference is now being made to FIG. 26 showing cyclic voltammograms of the DNSP electrode after 16 mins. (curve (c) is at time t=0, curve z is at time t=16 mins.) incubation of the electrode with anti-DNP antibody. FIG. 26(a) shows results with an electrode wherein the antigen is in its original state (state (a) in FIG. 25), while FIG. 25(b) is an electrode in which the antigen was photoisomerized to the zwitterionic merocyanine configuration (state (b) in FIG. 25). The results clearly indicate that the antibody, which binds to the DNSP, insulates the electrode and decreases the electrical response. In comparison, the antibody does not actually bind to the inactive merocyanine isomer as is evident from the fact that the voltammogram remains almost unchanged as compared to the initial electrode response (curve c).

Reference is now being made to FIG. 27 showing the change in the amperometric response, versus control, at various electrode states. In each state, the electrode was incubated for 16 mins. with anti-DNP antibody. In this experiment the electrode was initially in a state wherein the immobilized antigen had the zwitterion merocyanine configuration (configuration (b) in FIG. 25). Following incubation with anti-DNA antibody, there is a high amperometric response (full dot, marked a) implying that the antibody does not actively interact with the immobilized antigen layer. Irradiation of the electrode at a wavelength above 480 nm, results in isomerization of the antigen to the spiropyran configuration (configuration (a) in FIG. 25). Incubation of this electrode with anti-DNP antibody for 16 mins. results in a decrease in the amperometric response of the electrode (empty square marked b) demonstrating the association of the antibody to the electrodes and its subsequent insulation. Further illumination at a wavelength between 300–400 nm results in conversion of the antigen layer back to the merocyanine configuration and in this state the electrode is again inactive towards anti-DNP antibody (full dot marked c): the high amperometric response of the resulting electrode implies that release of the antibody from the electrode surface has taken place. Further irradiation of the electrode at more than 480 nm converts the antigen back to the spiropyran configuration and the electrode can at this state again bind anti-DNP antibody (empty square marked d). Such an electrode can thus be used for repeated measurements.

EXAMPLE 7
Antigen-Antibody Recognition Pair (indirect mode)
Determination of Nε-2,4-DNP-Lysine by reaction with anti-DNP antibody and by the use of an electrode with an immobilized DNP layer The electrode preparation was carried out as described in Example 6, and illustrated in FIG. 25.

The agent solution was composed of 0.15M NaCl in phosphate buffer (0.01M, pH=7.4) and different concentrations of the antigen Nε2,4-DNP-lysine (having the formula 19 in FIG. 19). The analyte, anti-DNP-antibody (50 μM) was added to the agent solutions and mixed for 5 min. at 37±2° C.

The electrodes were illuminated with light, λ>450 nm, to ensure that the immobilized antigen monolayer will have the configuration (a) in FIG. 24. The electrode was then incubated in the antigen solutions for 18 min, washed with distilled water and used for electrochemical measurements.

The electrochemical measurements were performed in a three-electrode cell using the DNP-monolayer electrodes after treatment in the analyte solution, as the working electrodes, a Pt-wire as a counter electrode and Ag/AgCl as a reference electrode. The electrolyte was composed of 1.1 mM $K_4Fe(CN)_6$ being the redox molecule, and 0.15M NaCl in phosphate buffer solution (0.01M, pH=7.4). The temperature was 37±2° C., the scan rate was 200 mV/sec.

FIG. 27 shows the calibration curve of the electrode responses at different agent concentrations in the agent solution. $\Delta I_{pc}$ is the difference between the amperometric response of the antigen electrode in the presence of the redox probe only, and the response of the electrode after the treatment described above, with variable antigen concentrations.

EXAMPLE 8
Method for the modification of proteins by a group reactive to exposure to light energy The modification of the proteins by a group reactive to exposure to light energy was performed for example by carbodiimide coupling of the respective photoisomerizable active ester groups with the amino group of lysine residues which are a part of the protein molecule. The proteins that were modified by this method were Concanavalin A (Con. A), papain and chymotrypsin. The respective photoisomerizable active esters are N-hydroxysuccinimide ester of N-propionic acid spiropyran (formula 14 (a) and 15), N-hydroxysuccinimide ester of 4-carboxy azobenzene (16) and N-hydroxysuccinimide ester of thiophenefulgide (17) (the formulae are illustrated in FIG. 19).

The modification process was carried out by reacting 50 mg of the protein in 6 ml of an aqueous solution that contained 250 mg $NaHCO_3$ with 5–15 mg (according to the loading that is required) of the active ester dissolved in 200 μL of THF at 0° C. for 24–48 hours.

FIG. 28 shows an example of modification of Con A by linking to it a photoisomerizable compound. The active ester N-hydroxysuccinimide ester of thiophenefulgide (formula 17) was reacted with Con A and the resultant solution was centrifuged (15000 rpm, 30 min, 4° C.). The supernatant was then lyophilized to obtain a powder of modified protein. The loading degree was determined by conventional methods including absorbance measurements of the chromophore associated with the modified protein (ε2200 $cm^{-1}$, λ=532 nm) and determination of total protein content in the respective samples by the Lowry method (Lowry, O. H. et al., *J. Biol. Chem.* 103, 265 (1951)).

All modified proteins were capable of being converted from a first state to a second state and from the second state to the first in a substantially reversible manner and the states were followed spectroscopically.

EXAMPLE 9
Increasing Sensitivity
Increasing the sensitivity of anti-DNP-antibody analysis using an anti-IgE antibody An electrode with an immobilized layer of dinitrospiropyran (DNSP) was prepared by the method detailed in Example 6 and illustrated in FIG. 25. The DNSP electrode was challenged with a solution comprising 100 μM anti-DNP-antibody, for various periods of time, in which antigen-antibody pair complexes formed on the surface of the electrode. (The longer the time of incubation the higher is the amount of complex formation). The different electrodes were then electrochemically analyzed in the electrochemical cell described in Example 6. The amperometric response of the electrodes was recorded.

The electrodes were then incubated at 37° C. in a PBS buffer solution that contained 2.5 mg/ml of an anti-mouse IgE antibody for 10 mins. (The anti-DNP-antibody is a mouse Ige and the anti-mouse IgE thus forms a complex on the anti-DNP-antibody bound on the surface of the electrode). The electrodes were then transferred to the electrochemical cell as detailed in Example 6 and the amperometric response of the electrodes was recorded.

Reference is now being made to FIG. 1 in which $\Delta i^{(1)}_{pc}$ represents the change in the amperometric response of the electrode after it was challenged with the anti-DNP-antibody (as compared to the response prior to this challenge) and $\Delta i^{(2)}_{pc}$ represents the change in the amperometric response after the second challenge with the anti mouse IgE antibody. As can be seen in this figure, the values of $\Delta i^{(1)}_{pc}$ (X-axis) and the value of $\Delta i^{(2)}_{pc}$ (Y-axis) show a linear interrelation. The slope of this plot represents the enhancement factor of the electrode sensitivity following a challenge with the anti-IgE antibody. In this case the sensitivity was enhanced by a factor of about 2.3.

EXAMPLE 10
Use of an Electrode other than Gold

An electrode made of indium tin oxide (ITO) glass, is modified by incubating the electrode with a 1% (v/v) 3-amino propyltriethoxysilane with an organic solvent such as acetone, toluene or benzene. Following incubation, this linking group is immoblized on the electrode. Various antigens and proteins can then be immobilized through the amino residue of this linking group.

We claim:

1. An electrobiochemical system for determining the presence or concentration of an analyte in a liquid medium comprising:

an electrode, said electrode being made or coated with a metal selected from the group consisting of gold, platinum, silver and copper; or said electrode being made from conductive glass;

redox molecules dissolved in the liquid medium for exchanging electrons with said electrode;

means for generating and measuring an electrical response of said electrode; and, molecules immobilized on said electrode that bind to said analyte so as to form a recognition pair complex comprising an immobilized molecule and a molecule of said analyte, wherein said recognition pair complex impairs the electron exchange between said redox molecules and said electrode thereby decreasing said electrical response and allowing the presence or concentration of said analyte to be determined;

the immobilized molecule being immobilized on the surface of the electrode by means of a linking group having the following general formula:

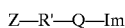

Z—R'—Q—Im wherein:

Z represents a sulfur containing moiety chemically associate with, attaching to, or chemisorption onto the electrode when the electrode is made or coated with said metal or Z represents methoxysilane or alkoxysilane residues which chemically associate with, attaching to, or chemisorption onto said conducting glass electrode;

R' represents a connecting group and Q is a functional group forming a covalent bond with the immobilized molecule represented by Im.

2. The system according to claim 1, wherein said recognition pair complex is selected from the group consisting of antigen-antibody, sugar-lectin, ligand-receptor, biotin-avidin, enzyme-substrate, oligonucleotide-DNA, oligonucleotide-protein, and oligonucleotide-cell.

3. The system according to claim 1, wherein said redox molecule is freely tumbling in solution.

4. The system according to claim 1, wherein the immobilized member of the recognition pair comprises a group reactive to exposure to light energy, said group having a first and a second state and converts from the first state to the second state by exposure to irradiation of light of a first wavelength and from the second to the first state by exposure to irradiation of light of a second wavelength, the exposure inducing a change in affinity of the immobilized member for binding to said analyte, whereby in the first state said immobilized member has a high affinity of binding to said analyte such that the analyte remains bound more tenaciously to the immobilized member than in said second state which incurs lower affinity state between said recognition pair.

5. A method for the determination of the presence and optionally the concentration of an analyte in a liquid medium, comprising the steps of:

(a) providing an electrode, said electrode being made or coated with a metal selected from the group consisting of gold platinum, silver and copper; or said electrode being made from conductive glass;

(b) providing redox molecules dissolved in the liquid medium for exchanging electrons to or from said electrode;

means for generating and measuring an electrical response of said electrode;

(d) providing molecules immobilized on said electrode that bind to said analyte so as to form a recognition pair complex comprising an immobilized molecule and a molecule of said analyte, wherein said recognition pair complex impairs the electron exchange between said redox molecules and said electrode thereby decreasing said electrical response and allowing the presence or concentration of said analyte to be determined;

the immobilized molecule being immobilized on the surface of the electrode by means of a linking group having the following general formula:

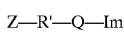

wherein:

Z represents a sulfur containing moiety chemically associating with, attaching to, or chemisorption onto the electrode when the electrode is made or coated with said metal or Z represents methoxysilane or alkoxysilane residues which chemically associate with, attach to, or chemisorption onto said conducting glass electrode;

R' represents a connecting group and Q is a functional group forming a covalent bond with the immobilized molecule represented by Im;

(e) contacting the electrode with the liquid medium;

(f) measuring the decrease in electrical response so as to determine the presence or concentration of the analyte in the medium.

6. The method according to claim 5, wherein said immobilized molecule bound to said analyte comprises a recognition pair that is selected from the group consisting of antigen-antibody, sugar-lectin, ligand-receptor, biotin-avidin, enzyme-substrate, oligonucleotide-DNA, oligonucleotide-protein, and oligonucleotide-cell.

7. The method according to claim 5, wherein the immobilized molecule has or is linked to a group reactive to exposure to light energy; said group having a first and a second state and is capable of being converted from the first state to the second state by exposure to irradiation of light of a first wavelength and from the second to the first state by exposure to irradiation of light of a second wavelength; the exposure inducing a change in affinity of the immobilized molecule for binding to said analyte, whereby in the first state said immobilized molecule has a high affinity of binding to said analyte such that the analyte remains bound more tenaciously to the immobilized molecule than in said second state which incurs lower affinity between the immobilized molecule and the analyte; the method comprising the following additional steps:

(g) irradiating said electrode by a light having said first wavelength;

(h) rinsing the electrode so as to remove analyte molecules from the medium surrounding the electrode; and (i) irradiating said electrode by light having a said second wavelength, whereby the electrode is ready for re-use.

8. The method according to claim 5, wherein the immobilized molecule comprises a photoreactive group, said group having a first and a second state and is capable of being converted from the first state to the second state by a mild thermal treatment; the exposure inducing a change in affinity of the immobilized molecule for binding to said analyte, whereby in the first state said immobilized molecule has a high affinity of binding to said analyte such that the analyte remains bound more tenaciously to the immobilized molecule than in said second state which incurs low affinity state between the immobilized molecule and the analyte, the method comprising the following additional steps:

(g) irradiating said electrode by a light having said first wavelength;

(h) rinsing the electrode so as to remove analyte molecules from the medium surrounding the electrode; and (i) subjecting the electrode to a mild thermal treatment, whereby the electrode is ready for re-use.

9. An electrode for use in the determination of the presence or concentration of an analyte, the analyte being a member of a recognition pair other than an enzyme-substrate pair, in a liquid medium, said electrode being made or coated with a metal selected from the group consisting of gold, platinum, silver and copper; or said electrode being made from conductive glass; so as to allow transport of electrons to or from a redox molecule and having immobilized thereon a layer of one member of said recognition pair other than the analyte, the immobilized member being immobilized on the surface of the electrode by means of a linking group having the following general formula:

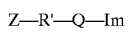

wherein

Z represents a sulfur containing moiety capable of chemical association with, attachment to, or chemisorption onto the electrode when the electrode is made or coated with said metal or Z represents methozysilane or alkoxysilane residues which are capable of chemical association with, attachment to, or chemisorption onto said conducting glass electrode;

R' represents a connecting group and Q is a functional group forming a covalent bond with the immobilized member represented by Im, such that, binding of analyte to the immobilized member, modifies electron exchange between a redox molecule and said electrode whereby the presence or concentration of said analyte in a medium surrounding the electrode is determined.

10. A reusable electrode for use in an electro-chemical system for the determination of the presence or concentration of an analyte in a liquid medium, the electrode comprising:

an electrode material capable of electrical communication with a redox molecule; there being immobilized on the electrode material a layer of a member of a recognition pair the other member of the pair being said analyte: the electrical communication between the redox molecule and the electrode material being modified by binding of said member to said analyte;

the immobilized member has or is linked to a group reactive to exposure to light energy, said group having a first and a second state and is capable of being converted from the first state to the second state by exposure to irradiation of light of a first wavelength and from the second to the first state by exposure to irradiation of light of a second wavelength;

the exposure inducing a change in affinity of the immobilized member for binding to said analyte, whereby in the first state said immobilized member has a high affinity of binding to said agent such that the bound analyte is not readily dissociated and in said second state said immobilized member has a low affinity of binding to said analyte, such that the bound agent is readily dissociated and can be removed from the system and the electrode can then be exposed to light of a second wavelength inducing a change to said first state, whereby the electrode will be ready for re-use, whereby the presence or concentration of said analyte in a medium surrounding the electrode can be determined.

11. A method for the determination of the presence or concentration of an analyte in a liquid medium comprising:

providing an electrode, said electrode being made or coated with a metal selected from the group consisting of gold, platinum, silver and copper; or said electrode being made from conductive glass;

placing an electrode in said liquid medium containing redox molecules for exchanging electrons with said electrode;

providing means for generating and measuring an electrical response of said electrode; providing immobilized molecules on said electrode, said molecules binding to at least one molecule of said analyte so as to form a recognition pair complex comprising said immobilized molecule and at least one molecule of said analyte, wherein said recognition pair complex reduces the electron exchange between the redox molecule and said electrode thereby changing said electrical response and allowing the presence or concentration of said analyte to be determined;

the immobilized molecule being immobilized on the surface of the electrode by means of a linking group having the following general formula:

Z—R'—Q—Im wherein:

Z represents a sulfur containing moiety chemically associating with, attaching to, or chemisorption onto the electrode when the electrode is made or coated with said metal or Z represents methoxysilane or alkoxysilane residues which chemically associate with, attach to, or chemisorption onto said conducting glass electrode;

R' represents a connecting group and Q is a functional group forming a covalent bond with the immobilized molecule represented by Im; and measuring the change in electrical response and based thereon determining the presence or concentration of said analyte.

12. A method for the determination of the presence or concentration of an analyte in a liquid medium comprising:

providing an electrode, said electrode being made or coated with a metal selected from the group consisting of gold, platinum, silver and copper; or said electrode being made from conductive glass;

placing an electrode into said liquid medium containing analyte, said analyte molecules containing at least one redox moiety for exchanging electrons with said electrode;

providing means for generating and measuring an electrical response of said electrode; providing immobilized molecules on said electrode, said molecules binding to at least one molecule of said analyte so as to form a recognition pair complex comprising said immobilized molecule and at least one molecule of said analyte, wherein said recognition pair complex enhances the electron exchange between the redox molecule and said electrode thereby changing said electrical response and allowing the presence or concentration of said analyte to be determined;

the immobilized molecule being immobilized on the surface of the electrode by means of a linking group having the following general formula:

Z—R'—Q—Im wherein:

Z represents a sulfur containing moiety chemically associating with, attaching to, or chemisorption onto the electrode when the electrode is made or coated with said metal or Z represents methoxysilane or alkoxysilane residues which chemically associate with, attach to, or chemisorption onto said conducting glass electrode;

R' represents a connecting group and Q is a functional group forming a covalent bond with the immobilized molecule represented by Im; and measuring the change in the electrical response and based thereon determining the presence or concentration of said analyte.

13. An electrobiochemical system for determining the presence or concentration of an analyte in a liquid medium comprising:

an electrode;

redox molecules dissolved in the liquid medium for exchanging electrons with said electrode;

means for generating and measuring an electrical response of said electrode;

molecules immobilized on said electrode that bind to said analyte so as to form a recognition pair complex comprising an immobilized molecule and a molecule of said analyte;

the immobilized molecule being immobilized on the surface of the electrode by means of a linking group having the following general formula:

Z—R'—Q—Im wherein:

Z represents a sulfur containing moiety chemically associating with, attaching to, or chemisorption onto the electrode when the electrode is made or coated with metal or Z represents methoxysilane or alkoxysilane residues which chemically associate with, attach to, or chemisorption onto a conducting glass electrode;

R' represents a connecting group and Q is a functional group forming a covalent bond with the immobilized molecule represented by Im; and said recognition pair complex being selected from the group consisting of antigen-antibody, sugar-lecithin, ligand-receptor, biotin-aviden, enzyme-substrate, oligonucleotide-DNA, oligonucleotide-protein, and oligonucleotide-cell.

14. The system according to claim 13 wherein said redox molecule is freely tumbling in solution.

15. The system according to claim 13, wherein the electrode material is selected from the group consisting of gold, platinum, silver, copper and conducting glass.

16. The system according to claim 13 wherein the electrode is coated with a material selected from the group consisting of gold, platinum, silver, copper and conducting glass.

17. The system according to claim 13, wherein the immobilized member of the recognition pair comprises a group reactive to exposure to light energy, said group having a first and a second state and converts from the first state to the second state by exposure to irradiation of light of a first wavelength and from the second to the first state by exposure to irradiation of light of a second wavelength, the exposure inducing a change in affinity of the immobilized member for binding to said analyte, whereby in the first state said immobilized member has a high affinity of binding to said analyte such that the analyte remains bound more tenaciously to the immobilized member than in said second state which incurs lower affinity state between said recognition pair.

18. An electrobiochemical system for determining the presence or concentration of an analyte in a liquid medium comprising:

an electrode;

redox molecules dissolved in the liquid medium for exchanging electronic with said electrode;

means for generating and measuring an electrical response of said election;

molecules immobilized on said electrode that bind to said analyte so as to form a recognition pair complex comprising an immobilized molecule and a molecule of said analyte;

said molecule immobilized on said electrode comprises a group reactive to exposure to light energy, said group having a first and a second state and converts from the first state to the second state by exposure to irradiation of light of a first wavelength and from the second to the first state by exposure to irradiation of light of a second wavelength, the exposure inducing a change in affinity of the immobilized member for binding to said analyte, whereby the first in the first state said immobilized member has a high affinity of binding to said analyte such that the analyte remains bound more tenaciously to the immobilized pair than in the second state which has a lower degree of affinity between said recognition pair, and wherein said recognition pair complex impairs the electron exchange believed said redox molecules and said electrode thereby decreasing said electrical response and allowing the presence or concentration of said analyte to be determined.

19. A method for the determination and, optionally, the concentration of an analyte in a liquid medium comprising the steps of:

(a) providing an electrode, said electrode being made or coated with a metal selected from the group consisting of gold, platinum, silver and copper; or said electrode being made from conductive glass;

(b) redox molecule for transferring electrons with said electrode, and molecules, immobilized on said electrode, that bind to said analyte so as to decrease electron transfer with the electrode, (c) the immobilized molecule being immobilized on the surface of the electrode by means of a linking group having the following general formula:

Z—R'—Q—Im wherein:

Z represents a sulfur containing moiety chemically associating with, attaching to, or chemisorption onto the electrode when the electrode is made or coated with said metal or Z represents methoxysilane or alkoxysilane residues which chemically associate with, attach to, or chemisorption onto said conducting glass electrode;

R' represents a connecting group and Q is a functional group forming a covalent bond with the immobilized molecule represented by Im;

(d) reacting said liquid medium, or a fraction thereof, said liquid medium containing an agent, with a reagent either to yield an analyte or to cause a depletion in free analyte concentration, (e) contacting the electrode with a solution obtained from (b); and (f) measuring a change in electrical response resulting from contact of the electrode with the analyte, whereby the presence and optionally the concentration of said analyte said liquid medium is determined.

20. The method according to claim 19 wherein said liquid reagent contains an agent which is a molecule which is either (i) broken down by an enzyme into molecules, one of which is said agent (ii) being a precursor molecule which is converted by an enzyme to said agent;

said reagent solution further comprising said enzyme.

21. A system for determining the presence or concentration of an agent in a biological sample, comprising:

a reagent solution which in the presence of said agent causes either formation of an analyte or depletion of an a priori present analyte;

an electrode made or coated with a metal or said electrode being made from conductive glass;

redox molecules dissolved in the liquid medium for exchanging electrons with said electrode;

means for generating and measuring an electrical response of said electrodes; and molecules immobilized on said electrode that bind to said analyte so as to form a recognition pair complex comprising an immobilized molecule and a molecule of said analyte, wherein said recognition pair complex impairs the electronic change between said redox molecules and said electrode thereby decreasing said electrical response and allow to determine the presence or concentration of said analyte, serving as an indication for the presence or concentration of said agent in the biological sample, and the immobilized molecule being immobilized on the surface of the electrode by means of a linking group having the following general formula:

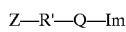

Z—R'—Q—Im wherein:

Z represents a sulfur containing moiety chemically associating with, attaching to, or chemisorption onto the electrode when the electrode is made or coated with said metal or Z represents methoxysilane or alkoxysilane residues which chemically associate with, attach to, or chemisorption onto said conducting glass electrode; and R' represents a connecting group and Q is a functional group forming a covalent bond with the immobilized molecule represented by Im.

22. A system according to claim 21, wherein said analyte can bind to said agent, the reagent solution comprising said analyte.

23. A system according to claim 22, wherein said agent is an antigen, said analyte is an antibody which binds to said antigen and the molecules immobilized on said electrode are antigens which bind to said antibody.

24. A system according to claim 22, wherein said agent is an antibody, said analyte is an antigen which binds to said antibody and the immobilized molecules on said electrodes are antibodies which bind to said antigen.

25. A system according to claim 21, wherein said agent is an enzyme which is capable of either breaking down the analyte into products which cannot bind to the molecules immobilized on the electrode, in which case the reagent system comprises the analyte, or is capable of catabolizing the analyte from precursor molecules, in which case said reagent solution comprises the precursor molecules.

26. A system according to claim 21, wherein said agent is a molecule which is either broken down by an enzyme into products, one of which being said analyte, or being a precursor molecule which is converted by an enzyme to said analyte, said reagent solution comprising said enzyme.

27. A method for determining the presence or concentration of an agent in a biological sample, comprising:

(a) reacting said sample or a fraction thereof comprising said agent if present in the sample with a reagent solution, whereby in the presence of an analyte either
 i. an analyte forms, or
 ii. an analyte already present is depleted so as to form a tested medium;

(b) providing an electrode, said electrode being made or coated with a metal selected from the group consisting of gold, platinum, silver and copper; or said electrode being made from conductive glass;

(c) redox molecules for transferring electrons to or from said electrodes, and molecules, immobilized on said electrode, that bind to said analyte so as to decrease electron transfer between the redox molecules and the electrode, thereby decreasing electrical response of the electrode;

(d) the immobilized molecule being immobilized on the surface of the electrode by means of a linking group having the following general formula:

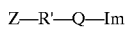

Z—R'—Q—Im wherein:

Z represents a sulfur containing moiety chemically associating with, attaching to, or chemisorption onto the electrode when the electrode is made or coated with said metal or Z represents methoxysilane or alkoxysilane residues which chemically associate with, attach to, or chemisorption onto said conducting glass electrode;

R' represents a connecting group and Q is a functional group forming a covalent bond with the immobilized molecule represented by Im;

(e) contacting the electrode with a solution comprising the tested medium and the redox molecules dissolved in the solution; and (f) measuring the decrease in electrical response so as to determine the presence or concentration of the analyte in said liquid solution, and deducing therefrom the presence or concentration of said agent in the biological sample.

28. A method according to claim 27, wherein said analyte can bind to said agent, said reagent solution comprising said analyte.

29. A method according to claim 28, wherein said agent is an antigen, said analyte is an antibody which binds to said antigen and the immobilized molecules on said electrodes are antigens which bind to said antibody.

30. A method according to claim 27, wherein said agent is an antibody, said analyte is an antigen which binds to said antibody and the immobilized molecules on said electrode are antibodies which bind to said antigen.

31. A method according to claim 27, wherein said agent is an enzyme which is capable of either breaking down the analyte into products which cannot bind to the molecules immobilized on the electrode, in which case the reagent system comprises the analyte, or is capable of catabolizing the analyte from precursor molecules, in which case said reagent solution comprises the precursor molecules.

32. A method according to claim 27, wherein said agent is a molecule which is either broken down by an enzyme into products, one of which being said analyte, or being a precursor molecule which is converted by an enzyme to said agent, said reagent solution comprising said enzyme.

* * * * *